United States Patent
Little et al.

(10) Patent No.: US 11,357,413 B2
(45) Date of Patent: Jun. 14, 2022

(54) METHODS AND APPARATUS FOR SELF-CALIBRATING NON-INVASIVE CUFFLESS BLOOD PRESSURE MEASUREMENTS

(71) Applicant: HEALTHY.IO LTD., Tel Aviv-Jaffa (IL)

(72) Inventors: Max Little, Oxford (GB); Martin Zizi, Enines (BE); Ivo Clarysse, San Francisco, CA (US); Bernard Burg, Menlo Park, CA (US); Abel Villca Roque, Dublin, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 574 days.

(21) Appl. No.: 16/294,432

(22) Filed: Mar. 6, 2019

(65) Prior Publication Data

US 2019/0307337 A1    Oct. 10, 2019

Related U.S. Application Data

(63) Continuation of application No. 14/641,303, filed on Mar. 6, 2015, now abandoned.
(Continued)

(51) Int. Cl.
*A61B 5/021* (2006.01)
*A61B 5/026* (2006.01)
(Continued)

(52) U.S. Cl.
CPC ........ *A61B 5/02141* (2013.01); *A61B 5/0261* (2013.01); *A61B 5/0295* (2013.01);
(Continued)

(58) Field of Classification Search
CPC . A61B 5/02141; A61B 5/0261; A61B 5/0295; A61B 5/282; A61B 5/316;
(Continued)

(56) References Cited

U.S. PATENT DOCUMENTS

| | | | | | |
|---|---|---|---|---|---|
| 4,869,262 | A | * | 9/1989 | Orr | A61B 5/021 600/485 |
| 2005/0234363 | A1 | * | 10/2005 | Xue | A61B 5/349 600/515 |

(Continued)

FOREIGN PATENT DOCUMENTS

CN          103027690 A  *  4/2013

OTHER PUBLICATIONS

Veerabhadrappa S. T., Anoop Lal Vyas, and Sneh Anand, "Estimation of Pulse Transit Time using Time Delay Estimation Techniques", 4th International Conference on Biomedical Engineering and Informatics (BMEI), p. 739-743, 2011 (Year: 2011).*

(Continued)

*Primary Examiner* — Allen Porter
*Assistant Examiner* — Abid A Mustansir
(74) *Attorney, Agent, or Firm* — Finnegan, Henderson, Farabow, Garrett & Dunner, LLP

(57) ABSTRACT

In one embodiment of the invention, a non-invasive method of measuring blood pressure is disclosed. The method includes scanning for ECG data with a portable cuffless blood pressure measuring device including, forming an electronic circuit with a first electrode and a second electrode of the portable cuffless blood pressure measuring device by contacting the first electrode with a user's temple and contacting the second electrode with the user's finger holding the portable cuffless blood pressure measuring device; concurrently scanning for PPG data with the cuffless blood pressure measuring device during ECG scanning by (Continued)

placing the PPG sensor to the user's temple; cross-correlating the ECG data and the PPG data to determine a PWTT for the user; receiving one or more physiological data of the user; and using regression analysis to predict systolic blood pressure of the user in response to the PWTT and the one or more physiological data.

13 Claims, 25 Drawing Sheets

Related U.S. Application Data

(60) Provisional application No. 61/988,899, filed on May 5, 2014, provisional application No. 61/949,235, filed on Mar. 6, 2014.

(51) Int. Cl.
| | | |
|---|---|---|
| A61B 5/0295 | (2006.01) | |
| A61B 5/00 | (2006.01) | |
| A61B 5/282 | (2021.01) | |
| A61B 5/316 | (2021.01) | |
| A61B 5/332 | (2021.01) | |
| A61B 5/333 | (2021.01) | |

(52) U.S. Cl.
CPC ............. *A61B 5/282* (2021.01); *A61B 5/316* (2021.01); *A61B 5/332* (2021.01); *A61B 5/333* (2021.01); *A61B 5/6814* (2013.01); *A61B 5/6826* (2013.01); *A61B 5/7203* (2013.01); *A61B 5/7246* (2013.01); *A61B 5/7267* (2013.01); *A61B 2560/0223* (2013.01); *A61B 2560/0425* (2013.01); *A61B 2560/0468* (2013.01); *A61B 2562/0209* (2013.01); *A61B 2562/0238* (2013.01); *A61B 2562/06* (2013.01); *A61B 2576/00* (2013.01)

(58) Field of Classification Search
CPC ..... A61B 5/332; A61B 5/6814; A61B 5/6826; A61B 5/7203; A61B 5/7267; A61B 5/145
See application file for complete search history.

(56) References Cited

U.S. PATENT DOCUMENTS

| | | | | |
|---|---|---|---|---|
| 2008/0249382 | A1* | 10/2008 | Oh ..................... | A61B 5/02125 600/324 |
| 2009/0326386 | A1* | 12/2009 | Sethi ................... | A61B 5/7278 600/480 |
| 2010/0217099 | A1* | 8/2010 | LeBoeuf .............. | A61B 5/4812 600/301 |

OTHER PUBLICATIONS

N.A. Zakaria, N.B. Sharifmuddin, W.M.F. Wan Mohd. Ridzwan, and N.H. Mahmood, "Pulse Wave Transit Time and Its Relationship with Systolic Blood Pressure", IFMBE Proceedings 31, pp. 1354-1357, 2010 (Year: 2010).*

* cited by examiner

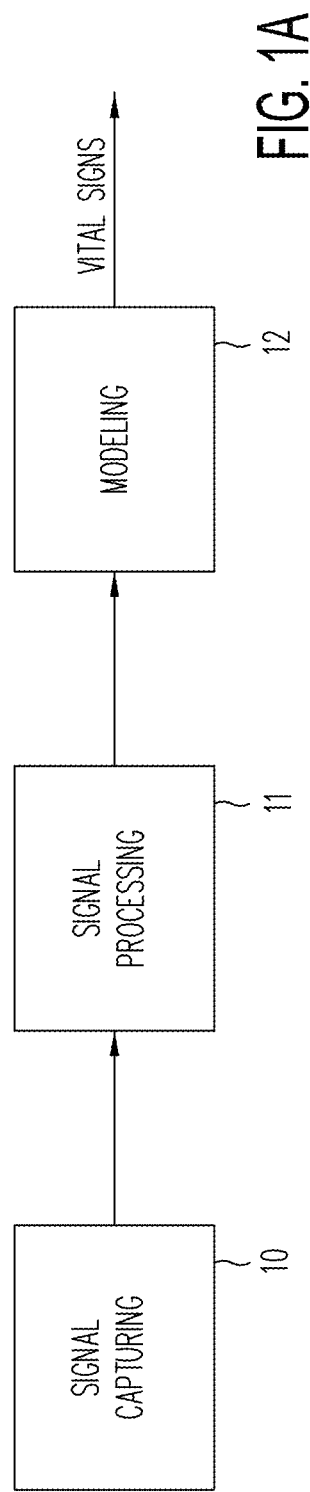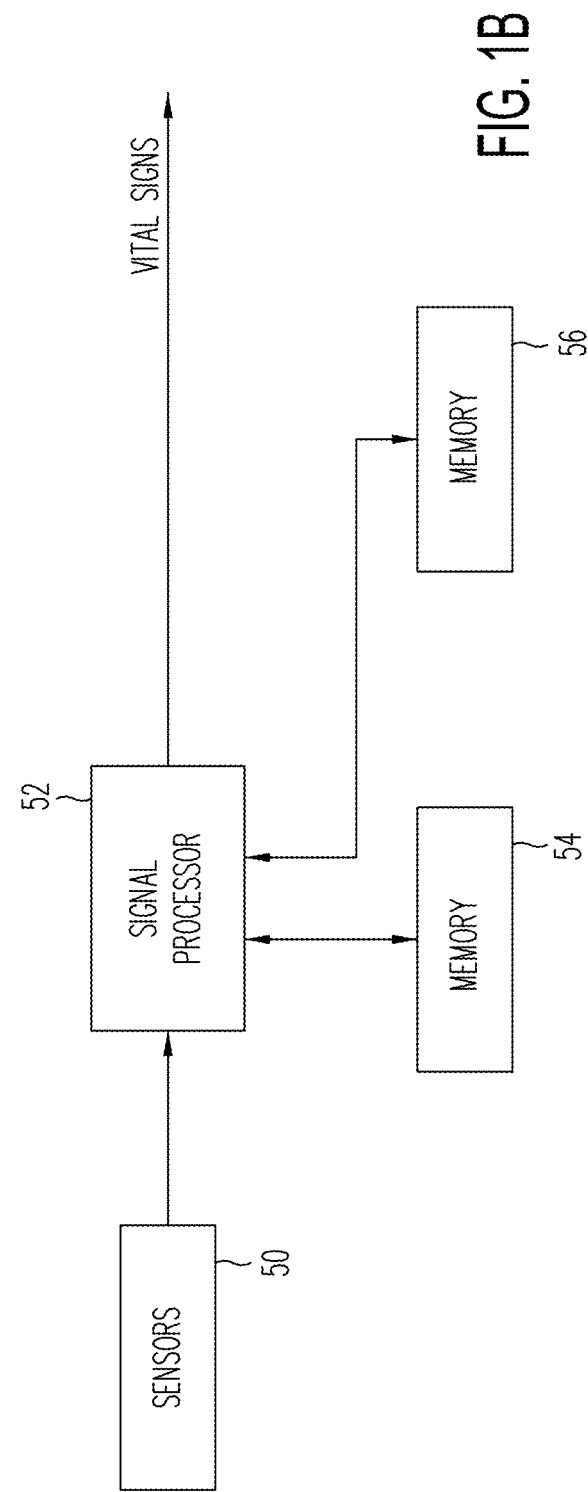

KEY TO

| $M^T$ | $X$ |
|---|---|
| A | $X_1$ |
| H | $X_2$ |
| ECG | $X_3$ |
| ECG_SL | $X_4$ |
| PPG_WS | $X_5$ |
| PPG_SL | $X_6$ |
| PWTT | $X_7$ |
| $A_h$ | $Xh_1$ |
| $H_h$ | $Xh_2$ |
| $ECG_h$ | $Xh_3$ |
| $ECG\_SL_h$ | $Xh_4$ |
| $PPG\_WS_h$ | $Xh_5$ |
| $PPG\_SL_h$ | $Xh_6$ |
| $PWTT_h$ | $Xh_7$ |
| $A_g$ | $Xg_1$ |
| $H_g$ | $Xg_2$ |
| $ECG_g$ | $Xg_3$ |
| $ECG\_SL_g$ | $Xg_4$ |
| $PPG\_WS_g$ | $Xg_5$ |
| $PPG\_SL_g$ | $Xg_6$ |
| $PWTT_g$ | $Xg_7$ |

FIG. 14

METHODS AND APPARATUS FOR SELF-CALIBRATING NON-INVASIVE CUFFLESS BLOOD PRESSURE MEASUREMENTS

CROSS REFERENCE TO RELATED APPLICATIONS

This patent application is a continuation and claims priority to United States (US) non-provisional patent application Ser. No. 14/641,303, entitled METHODS AND APPARATUS FOR SELF-CALIBRATING NON-INVASIVE CUFFLESS BLOOD PRESSURE MEASUREMENTS filed by inventors Max Little et al., on Mar. 6, 2015. U.S. patent application Ser. No. 14/641,303 claims priority to U.S. provisional patent application No. 61/949,235, entitled SELF-CALIBRATING NON-INVASIVE CUFFLESS BLOOD PRESSURE MEASUREMENT METHOD AND DEVICE filed by inventors Max Little et al., on Mar. 6, 2014; and U.S. provisional patent application No. 61/988,899; entitled PORTABLE DEVICE WITH MULTIPLE INTEGRATED SENSORS FOR VITAL SIGNS SCANNING filed by inventors Bernard Burg et al., on May 5, 2014; both of which are incorporated herein by reference for all intents and purposes.

FIELD

The embodiments of the invention generally relate to methods and apparatus for measuring human blood pressure.

BACKGROUND

There are a number of techniques for measuring human blood pressure, but the most prominent and well-used technique is with a manual sphygmomanometer. A sphygmomanometer comprises an inflatable 'cuff' which is worn around some extremity, typically the upper arm, which, when inflated, restricts the flow of blood through an artery (for the arm, the brachial artery). The cuff is inflated using a pump, and a pressure meter is connected in-line with the pump, so that the pressure being exerted on the artery is known.

When measuring blood pressure, the manual sphygmomanometer inflates the cuff so as to restrict any blood flow into the artery. A stethoscope is placed over the artery downstream of the restriction created by the cuff. Initially there is no sound to be heard with the stethoscope because there is no blood flow. Decreasing the cuff pressure, leads to the emergence of sounds synchronous to the beats of the heart. The pressure level at which these sounds occur is the systolic blood pressure. These sounds occur because liquid flowing through a constriction becomes turbulent and creates many tiny 'vortices', which create 'Korotkoff sounds'. Such turbulent sounds are absent when the blood flows freely into an artery that is not constricted. The cuff pressure is further lowered to a second pressure level where the 'Korotkoff' sounds vanish. This second pressure level is the diastolic blood pressure value. By this method with a manual sphygmomanometer and a stethoscope, a skilled operator can find a reliable estimate of blood pressures in the artery and is able to differentiate between the systolic (active pumping) and diastolic (passive) pressures on each cardiac cycle. Standardized schemes and training for performing these estimates have been developed in the medical profession. The precision needed for the medical use of such sphygmomanometer devices is defined in standard ANSI/AAMI SP10:2002/(R)2008.

The manual sphygmomanometric blood pressure measurement method is often considered to be the 'gold standard' method of determining blood pressure of a patient. However, it requires some expertise and training, and is dependent upon the hearing of the operator, which means that non-expert individuals, who want to know their own blood pressure, are unlikely to be able to reliably use this method. For this reason, automated sphygmomanometric devices have been developed.

The most common approach in automated sphygmomanometric devices is to dispense with the stethoscope and the detection of Korotkoff sounds altogether. Instead, an automated pump controls the inflation of the cuff, and the arterial pulse is detected by a very sensitive, automated pressure sensor in the device. The amplitude of the pulse changes with the cuff inflation pressure, and so, by monitoring the pulse amplitude, the device can provide estimates of arterial blood pressure. Such devices try to circumvent the need for much of the expertise and training required for manual sphygmomanometry. These automated sphygmomanometric devices, however simple, can be error-prone as motion of the arms during measurements, folding the elbow; poor positioning of the cuff, among other problems, can yield the incorrect blood pressure values.

While manual and automated cuff-based sphygmomanometry is effective and ubiquitous, it is cumbersome. The cuff-based sphygmomanometry devices have a bulky cuff and associated mechanical devices, such as pneumatic tubing and an inflation pump. Typical cuffs are around 6" by 12", although larger cuffs are needed for larger people, sometimes also requiring larger pumps. Also, the pumps are noisy, energy-hungry and supplying sufficient power usually requires frequent battery replacement in portable devices.

There are also some usability issues with cuff-based measurements of blood pressure. Some users dislike the squeezing sensation of the cuff around their arms during cuff contraction. Some users may feel some pain from the cuff pressure that around their arms. The blood pressure cuff is somewhat clumsy to operate, oftentimes require two people to operate. The cuff is often difficult to slide onto one's arm, particularly for lone elderly users with reduced flexibility. Elderly users often feel cold. They wear sweaters or jackets that need be removed for cuff-based measurements. Blood pressure cuffs are often bulky and difficult to carry around when traveling. Automated pumps for the blood pressure cuffs are noisy and highly visible making them difficult to use in privacy when away from one's home.

To overcome the inconveniences of a blood pressure cuff, cuffless sphygmomanometry may be considered. There are a few known cuffless blood pressure measurement methods. One method of cuffless blood pressure measurement combines photoplethysmography (PPG) and electrocardiography (ECG) methods together. PPG exploits the phenomena that light passing through or reflected off the skin, is substantially modified both in terms of constituent wavelengths and amplitudes, as blood pulses through the underlying vessels and capillaries. The PPG signal can accurately and reliably detect such pulses occurring in tissue local to the PPG light sensor. ECG measures the changing flow of electrical charge of the heart through the skin, which repeats once per cardiac cycle, allowing precision estimates of the time at which maximal pressure in the heart cavities is reached—this impulse event is the origin of the PPG pulse. By comparing the timing of this impulse between the heart and a peripheral measuring point using PPG, blood flow velocity is measured. Then, making certain assumptions about the fluid mechanical properties of blood and the mechanical properties of arteries and vessels, it is possible to indirectly measure blood pressure by invoking basic concepts from fluid dynamics such as, for example, Bernoulli's principle, or the relationship between flow velocity and arterial wall stiffness.

This method of ECG/PPG-based blood pressure measurement has the advantage over cuff-based methods that PPG and ECG sensors can be very small and lightweight: a miniature light emitting diode (LED) for illumination coupled with a semiconductor light sensor (such as a photodiode), and a pair of conductive skin contact pads will usually suffice. In total these devices typically weigh around 1 gram and would fit in a volume of less than 0.5" cubed. Thus, ECG/PPG measurement would seem highly suited to lightweight, portable, consumer, non-expert blood pressure measurement. There is also no fundamental impediment, as there is with a cuff, to measuring blood pressure almost continuously. Notwithstanding these intrinsic advantages, the method has never been deemed sufficiently reliable to meet clinical standards of measurement accuracy, largely because it is extremely sensitive to anatomical and blood flow variations.

Prior art methods of ECG/PPG-based blood pressure measurements require periodic re-calibration. This periodic re-calibration is a correction by reference to cuff-based or other different methods of blood pressure measurement. The term recalibration used herein refers to either an initial calibration or an iterative calibration that has to be done over and over again over time.

A common recalibration that is performed is with blood pressure cuffs or devices performing the same measurement while not technically being a blood pressure cuffs (such as a so-called 'pneumatic device', for example)

Another approach to recalibration is through the use of individual calibration charts. Sometimes these charts are generated with blood pressure measurement cuffs, other times a specific acquisition method is described. Acquisition of these recalibration charts is often very costly in time and/or in computational effort.

Other methods in the prior art use several sensors to minimize the influence of anatomical variation. These methods still require recalibration. Some of these methods focus on the principle of multiple measurements situated with known anatomical distances. Yet other methods describe sensor sites on the body, or placement of sensors on devices.

Blood pressure cuff based devices may undergo recalibration. U.S. Pat. Nos. 5,564,427; 6,547,740; 7,402,138; 7,455,643; 7,615,011; 8,591,428; 8,535,234; 8,560,245; and U.S. Pat. App. Pub. No. 2011/0054328 describe several instances of blood pressure monitoring, metabolic monitoring, and blood volume measurement apparati, all of which are based on the measurement of Pulse Wave Transit Time (PWTT also known as PTT in some of the prior art) using PPG. The reported results explore the—effect of administration of phenylephrine, blood removal and, pentobarbital administration to PWTT measurements and the relationship between PWTT and blood pressure. All of these measurements were aimed at refining the described methods. However, the general principle behind this family of apparati requires the use of a cuff-based blood pressure monitor to recalibrate the patented apparati.

Cuffless blood pressure measurement devices may undergo a recalibration that is similar to those of the cuff based blood pressure measurement devices. U.S. Pat. App. Pub. No. 2012/0190949; U.S. Pat. Nos. 8,475,370; and 8,602,997 describe a body-worn system for continuously and non-invasively measuring blood pressure. These systems use for recalibration a pneumatic cuff system that uses the arm to detect diastolic and systolic measurements. Even if this pneumatic cuff is not technically a blood pressure cuff, it has exactly the same inconvenience to users as a cuff, and it is functionally equivalent to a cuff.

U.S. Pat. App. Pub. No. 2012/0108985 presents the invention of a cuffless blood pressure monitor directly sensing blood pressure on the user's wrist. It measures an average blood pressure as well as diastolic and systolic blood pressure. This invention is mentioned here as a device equivalent to a blood pressure cuff, but it is not directly related to the embodiments of the invention. It is a mechanical contraption which is again functionally equivalent to a cuff.

Recalibration of a blood pressure measurement device may be specific to a user based on his/her individual data. However, oftentimes recalibration to a specific user cannot be used for other persons.

U.S. Pat. App. Pub. No. 2006/0047214 presents a wireless medical probe measuring core temperature, arterial pressure, arterial blood oxygenation and others. Blood pressure is determined by either method: using only ECG or PPG, or by time delay between PPG and ECG. Naturally, these methods require recalibration for each individual using conventional blood pressure measurements. However, no such recalibration method is described in U.S. Pat. App. Pub. No. 2006/0047214.

U.S. Pat. No. 6,599,251 describes a continuous non-invasive blood pressure monitoring method and apparatus. The method comprises detecting a pulse signal at a site on the subject and a subsequent pulse signal at another site on the subject. This is used to measure time differences between pulse arrival at corresponding sites. The estimated blood pressure is computed from time difference and relies on a personal recalibration based on either on previously stored data, or on systolic and diastolic blood pressures measured using a different device.

U.S. Pat. No. 5,873,834 entitled 'blood pressure detecting device' describes a method using a blood pressure cuff to initially recalibrate the PWTT, individually for each patient. The processing unit then stores an equation converting the value of the physiological data to the corresponding blood pressure value. To determine this equation during the recalibration, the patient's physiological data is measured several times in the course of normal activities in order to obtain the blood pressure values individually for each patient.

U.S. Pat. App. Pub. No. 2010/0081946 presents 'Method and apparatus for non-invasive cuffless blood pressure estimation using pulse arrival time and heart rate with adaptive calibration'. As the title mentions, U.S. Pat. App. Pub. No. 2010/0081946 uses an adaptive recalibration process to control the precision of method and apparatus. This is an individual recalibration that must be done for each new user. The initial recalibration for the very first user needs about 40 measurements of systolic and diastolic blood pressure taken 5 minutes apart, therefore the recalibration for the very first user is estimated to require 3 hours and 20 minutes. For subsequent users, the proposed estimation algorithm can leverage acquired data using a linear prediction model and recalibrations of the system take approximately one hour for each new user. Once the system is recalibrated for a user, personal model parameters are automatically recalibrated at constant times using recursive least squares approach combining smoothing and bias fixing. Such a method is impractical for the lay user. The purely linear recalibration model may also limit accuracy.

Recalibration of a blood pressure measurement device may be specific to a user based on his/her individual data and an estimate of blood volume. U.S. Pat. Nos. 5,857,975 and 5,865,755 authored by H. Golub and assigned to DxTek Inc. do not mention the need for recalibration. The method protected by the patent is based on the Moens-Korteweg model, known to be very approximate, and in addition it uses 5 PPG measurements to derive the circulating blood volume per stroke. The derivative of these volume measurements is used to estimate blood pressure.

Experiments performed on twenty-eight intensive care unit (ICU) patients demonstrated the precision of the method for critically ill subjects, as reported in Heard et al. (Heard S O, Lisbon A, Toth I, Ramasubramanian R., An evaluation of a new continuous blood pressure monitoring system in critically ill patients, J Clin Anesth. 2000 November; 12(7): 509-18, available at http://www.ncbi.nlm.nih.gov/pubmed/ 11137411). However, as described in this study, the method protected by the patent requires precise recalibration for each individual, and in addition this recalibration depends on the precise location of measurement sites on the individual, as the choice of these locations will markedly alter the volume calculations. In addition, the study details the necessity to recalibrate the method if the measurement site has changed even slightly. In the same study, it is clearly mentioned that the method required recalibration every 100 minutes, which is a huge improvement for an ICU patient but is far from practical in the vast majority of applications which are outside the ICU. Quote: "The number of calibrations needed for the DxTek is higher than that required for arterial catheters. Accurate BP determination is dependent on obtaining a good optical plethysmography signal; thus, in the agitated patient, the frequency of the device reporting that no pressure is possible due to artifact may be high. However, the fact that the average time between recalibrations was 100 minutes suggests that this method of measuring BP is not readily undermined".

Moreover it is clear to those skilled in the art that the methods disclosed in U.S. Pat. Nos. 5,857,975 and 5,865, 755 cannot cope with the noise inherent in signals captured by active users taking self-measurements with small handheld scanning devices. In these more realistic conditions, experiments and the literature show that blood volume estimation methods are unable to reach the desired clinical precision.

Another approach to blood pressure measurements is to use several sensors. U.S. Pat. No. 7,674,231 describes a wearable pulse wave-velocity blood pressure sensor. It discloses methods of recalibration based on two PPG sensors performing circulatory measurement on a single hand. The recalibration relies on time differences between the two PPG measurements recorded on an extremity of the user. Despite the two PPG measurements, the recalibration of the device remains problematic with three different solutions to recalibration being proposed. The first approach is to use an additional blood pressure cuff. The second method proposed relies on arterial wall compliance simulation The third proposed method relies on pressure derivative or pulse wave velocity. The latter two methods of recalibration are highly sensitive to noise in the recorded signals, and thus are typically discarded.

In European Pat. No. EP2644089 ("Blood pressure estimation using a hand-held device"—also filed as WO/2013/ 144968), ECG and PPG, and derived PWTT measurements are taken from both hands. It proposes eight methods to calculate blood pressure when measuring PWTT. Methods 1, 6, 7, and 8 are well known in the prior art. These well known methods provide low precision such that no device using these methods has yet reached clinical precision. Clinical precision requires a maximum mean error of ±5 mmHg and maximum standard deviation of 8 mmHg for systolic and diastolic blood pressure measurements. See method 1 of the standard ANSI/AAMI SP10:2002/(R)2008, Section 4.4.5.1.B. See also AAMI/ANSI/IS081060-2 $2^{nd}$ Edition, 2013-05-01. An accurate measurement is a trade-off between bias against variance. Methods 2 to 5 of European Pat. No. EP2644089 use an external calibration process, typically provided by a blood pressure cuff. Accordingly, the methods of recalibration disclosed in EP2644089 tend to be unreliable.

U.S. Pat. App. Pub. No. 2013/0184595 describes methods and apparati for determining the arterial pulse wave and pulse wave velocity. This requires two measurement sites on a user but does not disclose estimating blood pressure.

U.S. Pat. No. 6,331,162 is also a pulse wave velocity measuring device that requires two transducers placed on the thoracic aorta: precisely, on the fourth thoracic vertebra and the second lumbar vertebra. U.S. Pat. No. 6,331,162 requires exact positioning of the sensors so that the resulting signal is clean. However, U.S. Pat. No. 6,331,162 does not disclose estimating blood pressure. Moreover, in practice signals are noisy and precise placement of sensors by the user impractical.

Other methods may use several sensors at different sites or locations on a user's body. U.S. Pat. App. Pub. No. 2013/0261414 and U.S. Pat. App. Pub. No. 20110257535— related to EP2644089, focus on cardiac monitoring by recording ECG and PPG, deriving PWTT from both hands of the user.

With ECG recording, the number and position of leads to provide a clear signal may be important. In PPG recording, the position of the sensor may be even more important because pulse waves take time to propagate through a body, depending upon a complex topology and geometry of the vascular system. For example, European Pat. No. EP2644089 and its related. US patent documents, US Pat. App. Pub. No. 2013/0261414 and U.S. Pat. App. Pub. No. 20110257535, describe positioning ECG leads for two hands and the positioning of PPG to be taken on both hands, with the user holding the device between thumb and index finger, and thumb and middle finger.

U.S. Pat. No. 8,615,290 describes positions of ECG leads on the bezel of a heart rate monitor, placing three leads into the device. The patent claims the position of the leads in the bezel of the device but does not mention which body parts are to be placed in contact with these bezels.

U.S. Pat. No. 5,497,778 describes apparatus for noninvasive measurement of peripheral pressure pulse compliance and systolic time intervals. This device takes carotid pulse wave input and compares it to ECG input to assess vascular compliance and peripheral resistance of a subject. However, there is no attempt to measure blood pressure with the apparatus disclosed in U.S. Pat. No. 5,497,778.

There are a number of miscellaneous prior art references that are related to blood pressure measurements. For example, U.S. Pat. App. Pub. No. 2004/0015091 entitled 'System and method of assessment of arousal, pain and stress during anesthesia and sedation' describes a system including ECG and PPG probes connected to a computer. The system estimates the user's PWTT from heart to hand for each heartbeat. The estimated PWTT and its derivative in time (rate of change of PWTT) are displayed numerically for interpretation by clinicians. US Pat. App. Pub. No. 2004/0015091 is not directly relevant to the embodiments of the invention as the technology involved is different. This patent is cited for completeness of search of the prior.

U.S. Pat. App. Pub. No. 2013/0123617 describes a method and apparatus for the non-invasive measurement of PWTT. This method exploits electric impedance tomography images. Due to this very specific sensor, there is no overlap between the embodiments of the invention and the methods and apparatus presented in U.S. Pat. App. Pub. No. 2013/0123617. This patent is cited for completeness of prior art search, and its technological solution is entirely different from the embodiments of the invention.

U.S. Pat. No. 7,559,894; entitled MULTIPARAMETER WHOLE BLOOD MONITOR AND METHOD; presents a method for continuous intravascular, blood pressure and pulse pressure measurement. An intravascular catheter incorporates a sensor to measure whole blood sound velocity, attenuation, backscatter amplitude, and blood flow velocity using the Doppler effect. The methods and apparatus disclosed in U.S. Pat. No. 7,559,894 are invasive. A non-invasive method and apparatus for measuring blood pressure is desirable.

In general, the accuracy and reliability of a combined ECG/PPG-based blood pressure measurement has been problematic in commercial devices. The prior methods of measuring blood pressure inherently lack reliability, are not validated to clinical grade because their accuracy falls outside mandated clinical measurement error tolerances. ECG/PPG-based blood pressure devices are generally used after a recalibration phase using cuff-based blood pressure measurement. Recalibration with cuff-based blood pressure measurement undermines the practical utility of the devices.

The prior methods of measuring human blood pressure either require recalibration or a cuff. Additionally, the prior methods of blood pressure measurements may use different pulse measurement locations on a human body, or different pulse measurements methods.

SUMMARY OF THE INVENTION

Generally disclosed are a method and a user device for performing non-invasive, quantitative measurement of blood pressure (diastolic and systolic) without using a blood pressure cuff or any pneumatic system, nor any external source or method of recalibration.

The embodiments of the invention provide a self-calibrating and cuffless method capable of recording blood pressure measurements to within the required tolerances described in the American National Standards Institute/Association for the Advancement of Medical Instrumentation standard (see e.g., AAMI/ANSI/ISO81060-2 $2^{nd}$ Edition 2013-05-01), currently adopted by the United States federal Food and Drug Administration for clinical usage.

The embodiments of the invention combines three steps to reach high precision in measurement as well as ease of use, such that users do not need to wear a cuff, nor do they need to wear any other apparati for any length of time. The user places the vital signs scanning device on his/her temple (or forehead) for a short period of time (e.g., ten seconds). Vital sign measurements can be performed with the vital signs scanning device in a very discreet and private manner, even in public settings. The vital signs scanning device is small enough to fit in the users hand to performs the vital signs measurement, without emitting any noise or visible signal.

Vital signs may be measured at different locations on a user's body. The embodiment of the invention measure photoplethysmogram (PPG) from a user's temple or forehead. Electrocardiogram (ECG or EKG) data is captured between two electrodes, one electrode on the temple or forehead and another at the tip of the finger holding the device to the temple/forehead. Measuring PPG at the temple takes advantage of human anatomy. There are fewer variations in physiological proportions between thorax/head than length of arms, which are directly proportional to height. Consequently, there are less anatomical variations and hence smaller physiological variability in PWTT and other derived measurements between individuals for two reasons: the artery from heart to temple is shorter than from heart to wrist, and it is not subject to as severe pressure drops as compared to measurements performed on the arms or wrists which vary in a complex way according to many factors, for example, the geometric configuration of the arms, and the tension in the bulkier muscle groups such as the triceps and deltoids.

Additionally, the arterio-venous anatomical relationships in the arms are such that the arterial blood flow towards the extremities is used to regulate the temperature of the blood flow returning to the core of the body. While this leads to a beneficial heat exchange to protect the stability of the core temperature, this is an additional factor in the variation of arterial blood flow. Because the brain temperature needs to be protected, such temperature regulation mechanism is absent for the carotid and vertebral arterial basin. Hence, blood perfusion towards the brain is protected. Thus, the location of the sensor on the head contributes towards higher accuracy in the embodiments of the invention, as compared to the methods and devices described in the prior art, most of which measure PPG on the arms, wrists or hands. Human variability in arm lengths and in arm geometric configurations introduces large perturbations into the measurements performed at hands and arms, which is one of the main reasons why the prior art needs recalibration against cuff measurements.

More accurate, robust and complete derivations of critical physiological quantities from the recorded signals. The prior art focuses on the extraction of only one main quantity from the PPG and ECG signals, the PWTT, but this quantity alone does not suffice to determine blood pressure. PWTT is used in the determination of blood pressure, and it is desirable to be robust to overcome measurement noise. In this regard, the approach to extracting PWTT by the embodiments of the invention, use advanced nonlinear filtering to remove measurement noise without spreading the timing of critical cardio-analytic events, and a cross-correlation function between PPG and ECG that can readily achieve sub-millisecond precision.

This cross-correlation approach has two principle advantages. It is highly robust to noise or distortions in either PPG or ECG signal because it integrates over a large time interval, and it enables much higher accuracy timing extraction than the sampling interval of the digitized PPG or ECG signals would normally allow, by using appropriate analytical functions. Accurate PWTT is necessary, but additionally, in this invention, several novel measurements not found in the prior art are extracted from the PPG and ECG signal, including gross features of the power spectrum of both signals. One particularly important and novel quantity extracted in this invention and not in the prior art, is the PPG wave shape, which is known to be related to the strength of the reflectance of the pressure pulse at the primary arterial branches, and is thus related to arterial wall stiffness. Arterial stiffness is known, in turn, to be related to conditions such as atherosclerosis, which are important systematic factors leading to variation in blood pressure which confound the determination of blood pressure from PWTT alone. Indeed, one of the reasons why the prior art requires constant recalibration is that they do not extract sufficient information from PPG and ECG signals to uniquely determine blood pressure.

After an initial training/calibration, the methods employed by the embodiments of the invention to measure human blood pressure are self-calibrating. It uses mathematical relationships, which are known to hold, on the basis of broad physical principles, between quantities extracted from the PPG and ECG signals. By combining these broad physical relationships with advanced statistical machine learning techniques, it thereby extracts physiologically invariant components from the measured signal.

Prior models are typically too simple or too complex to adequately capture the full sources of variability, which occur in real, practical PPG and ECG signal measurement. Prior models often ignore underlying physiological variants. In contrast, the embodiments of the invention synthesize the available information needed to make a robust and precise determination of blood pressure. This information can include population-scale curated relationships between important quantities such as age, gender, height, weight, and body-mass index, to enhance the precision of the final blood pressure measurements. The model employed by the embodiments of the invention is not limited to incorporating the information listed above, because it is flexible enough that any relevant parameter, quantities related to orthoparasympathetic balance, or others, such as skin temperature for example, can readily be used to improve blood pressure measurements.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIG. 1A is a function block diagram of an embodiment of the invention.

FIG. 1B is a function block diagram of the signal processing system within a vital signs scanner in accordance with an embodiment of the invention.

FIG. 14 illustrates the transpose of a matrix M ($M^T$) and a matrix X in table form.

DETAILED DESCRIPTION

Figure 1C:
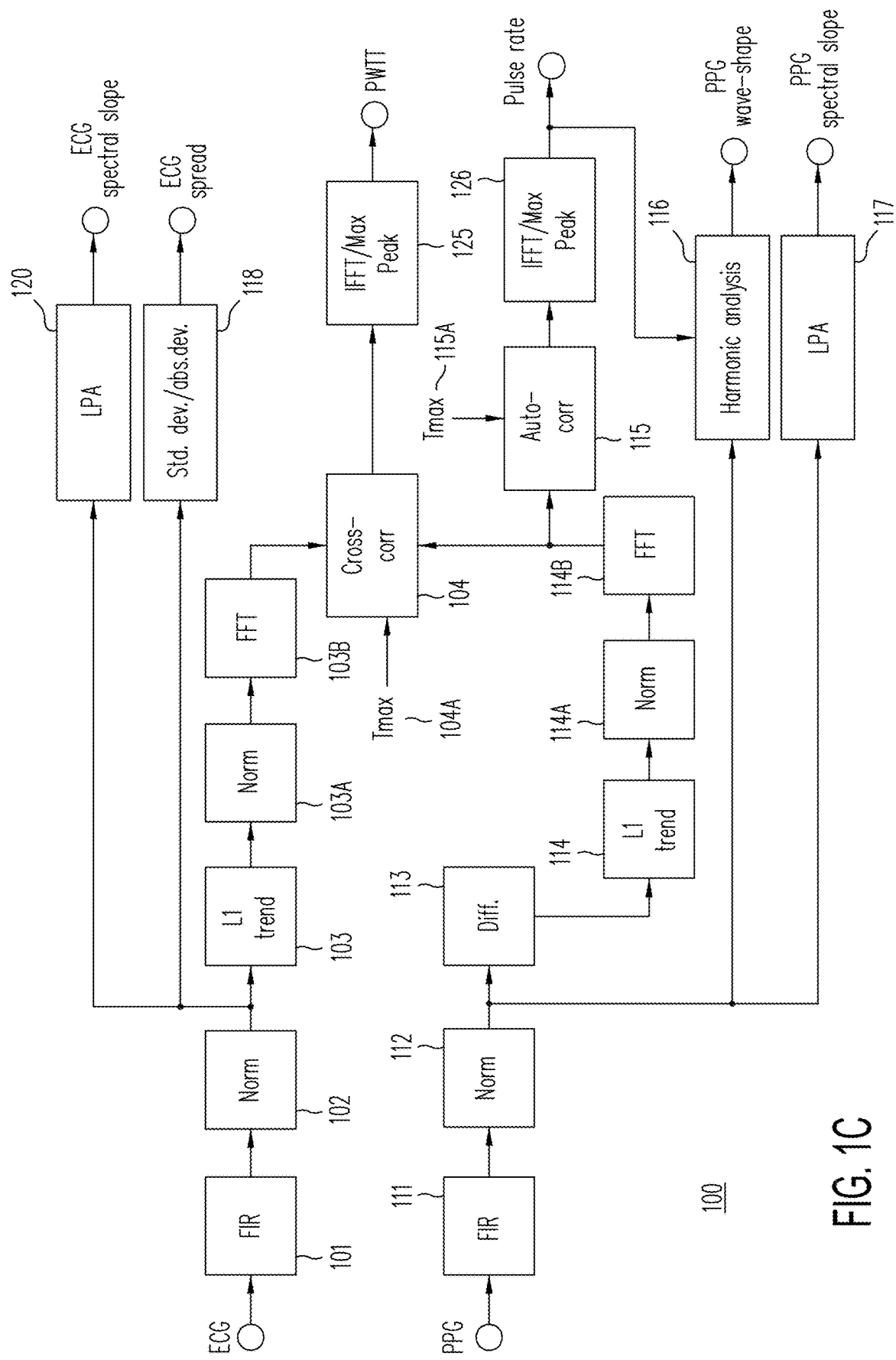
FIG. 1C is a function block diagram of an embodiment of the invention illustrating an exemplary method of sensor feature extraction by signal processing.

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more particular embodiments may also be included in combination with another embodiment even though not expressly shown and described in that specific combination.

For purpose of efficiency, reference numbers may be repeated between the figures where they are intended to represent similar features between otherwise varied embodiments, though those features may also incorporate certain differences between embodiments if and to the extent specified as such or otherwise apparent to one of ordinary skill (such as differences clearly shown between them in the respective figures).

There are many causes for the inaccuracy of the ECG/PPG-based methods of blood pressure measurements. Some of the more important confounding factors are as follows.

Blood flow velocity must be inferred from the time delay of the blood impulse travelling from the heart to the peripheral vessels and capillaries. This, however, is only possible if we know the physical dimensions involved: in particular, we need to know the length of the vascular path from the heart to the location of the PPG sensor. This is nearly always unknown in practice, thus blood flow velocity inferences are subject to considerable unknown variation.

Assuming the vessel walls are entirely rigid the pulse of the blood flow would not affect their diameter. This assumption implies that flow velocity and time delay are reciprocally related to each other. This assumption, however, does not correspond to reality: vessel and capillary walls are highly elastic and flex in response to each pulse. Therefore, flow velocity and time delay are not simple reciprocals of each other, and again, this undermines the accuracy of inferring blood pressure from pulse delay time.

Another common, simplifying assumption is that vessel walls from individual to individual have the same 'stiffness'. This is, however, untrue. As one ages, vessel walls increase in stiffness due to basic physiological aging processes such as the degradation of the extracellular matrix and of proteins such as collagen and elastin, all of which are fundamental to maintaining the elasticity of the vessel walls. Therefore, elderly vascular systems will, all other things being equal, have far stiffer blood vessel walls than younger systems. This uncertainty about physiological stiffness further undermines the accuracy of ECG/PPG-based blood pressure measurement. For analogous, but different reasons, females will have arterial wall stiffness differing from males. Accordingly, gender will be a factor in the physiological inputs and the selection of The vascular system is not a passive set of unresponsive mechanical tubes down which blood is pumped. The vascular system is actively able to change shape in response to circumstances the organism is facing. Smooth muscles line the walls of the arteries and other vessels, allowing them to constrict or dilate according to the circulation of hormones such as adrenaline, which are in a constant state of flux. Therefore, the diameter of the vessels is also constantly changing and this, in turn, modifies the blood flow velocity in ways, which are difficult to quantify precisely.

These issues can make ECG/PPG-based blood pressure measurements unreliable. Basic physical models such as the Bernoulli equation found in the prior art are far too simple.

One prior approach to try is to incorporate all of these main confounding effects, which hamper the accurate measurement of blood flow velocity, into a more sophisticated physical model. Then, the parameters of the model are estimated from measured data (for example, incorporating the Moens-Korteweg relationship between vessel wall arterial elastic modulus and blood flow velocity, or the gross geometry of the cardiovascular system). However, in practice, there are far too many free parameters in these models which must be inferred. Typical measurements contain too much noise to derive or estimate accurate parameter values for the model. Accordingly, merely increasing the detail of a physical model does not mean that it is possible to provide better predictions. The accuracy of predictions from such a physical model is dependent upon the accuracy of the data which can be collected.

Another prior approach is to ignore the physical details altogether and use basic statistical techniques to try to associate measured pulse timing estimates against blood pressure measurements recorded using a reference technique. It is hoped that such techniques, which explicitly incorporate uncertainties due to noise in the data, will produce more accurate blood pressure predictions. Unfortunately, because such approaches ignore the fact that there is no such simple statistical relationship between pulse delay times and blood pressure, the resulting predictions have intolerably large uncertainties.

Embodiments of the invention utilize a solution in between these two extremes. The physical principles are basic and cannot be violated. For example, all other things being equal, a decrease in pulse delay time leads to higher blood pressure. Similarly, the existence of noise means that this is indeed a statistical problem. One cannot pretend, as in the physical models, that measured pulse delay timing is not subject to considerable fluctuations due to a multitude of interacting factors which might never be measurable. This strongly suggests that a sufficiently flexible physical model is required which is, at the same time, inherently statistical.

By measuring on the arterial vascular bed located on the head (forehead, temple, other head locations), one relies on a blood flow that is steadier, and more stable from a region at a distance from the heart cavities that is anatomically less variable.

Therefore, the approach taken in this invention is to use nonlinear, Bayesian or regularized statistical methods which are sufficiently flexible to model many of the physical features of the problem, and at the same time, handle the noise in the data. The model has inputs for basic information about the user, including physiological data such as age, height, weight, and gender. The model also has inputs for an additional range of features from the ECG/PPG data, such as the PPG wave shape, which is known to change according to arterial stiffness. The model includes flexible mathematical functions which can capture the physical relationship between decreasing pulse delay time and increased blood pressure, modified by the stiffening of the arteries due to normal aging partly measured by the PPG wave shape.

Extracting robust pulse-wave transit time (PWTT) from noisy ECG/PPG recordings is required. Unavoidable artifacts occur when measuring ECG/PPG from hand-held devices due to movement drift, muscle tremor noise, body position noises, power interference, and other independent random effects. Most PWTT heuristics are based on 'peak-picking' and explicit synchronization of these peaks between ECG/PPG. Because peaks are localized in time, these are highly sensitive to ECG/PPG artifacts making prior art PWTT estimates extremely unreliable.

The embodiments of the invention introduce a cross-correlation between nonlinear filtered ECG/PPG. It integrates across the whole signal and so is robust to most localized measurement artifacts.

The time derivative of PPG is estimated to approximate the flow rate. In parallel the ECG signal is simplified by extracting its most important features relevant for timing. The QRS complex signal $q(t)$ is extracted from the ECG signal.

In accordance with one embodiment of the invention, statistical techniques of quasi-linear, L1-norm regularized regression is used to synthesize together a range of quantities extracted from both the PPG and ECG signals, including PPG wave shape, PPG power spectral decay, PPG pulse rate, and ECG/PPG pulse delay time using cross-correlation. Physiological inputs include subject age, approximate weight and height. The parameters of the model are estimated from training data associating the input data with a set of cuff-based measurements (the "gold-standard") using standard convex optimization techniques. The regularization parameter is estimated using cross-validation. Once these parameters are estimated, they need not be repeated.

Referring now to FIGS. 1A-1B, a process for determining vital signs of a human user with a vital signs scanner is shown. An initial signal capturing process 10 occurs with a plurality of sensors 50 concurrently capturing a plurality of data signals.

The plurality of data signals undergo a signal processing process 11 with a signal processor 52. A memory 54 coupled to the signal processor 54 stores instructions of a signal processing algorithm of the signal processing process 11. The instructions of the signal processing algorithm are executed by the signal processor to perform the signal processing process 11 on the plurality of captured data signals. As part of the signal processing process 11, the signal processor 54 and signal processing algorithm may reduce noise in the data signal and transform waveforms of the data signals into useful waveforms. As part of the signal processing process 11, the signal processor 54 and the signal processing algorithm may further extract information or expected signal features from the plurality of data signals that can be used to form one or more vital signs.

The extracted signal features from the signal data may then be used to determine vital signs by undergoing a modeling process 12. The modeling process 12 may also be used to validate the extracted signal features. Instructions stored in a storage device, such as memory 56, executed by the signal processor 52 may be the basis for the model of the modeling process 12. The model of the modeling process 12 may be trained to each user so that it accurately determines vital signs for the given user.

Signal Processing

Figure 1D:
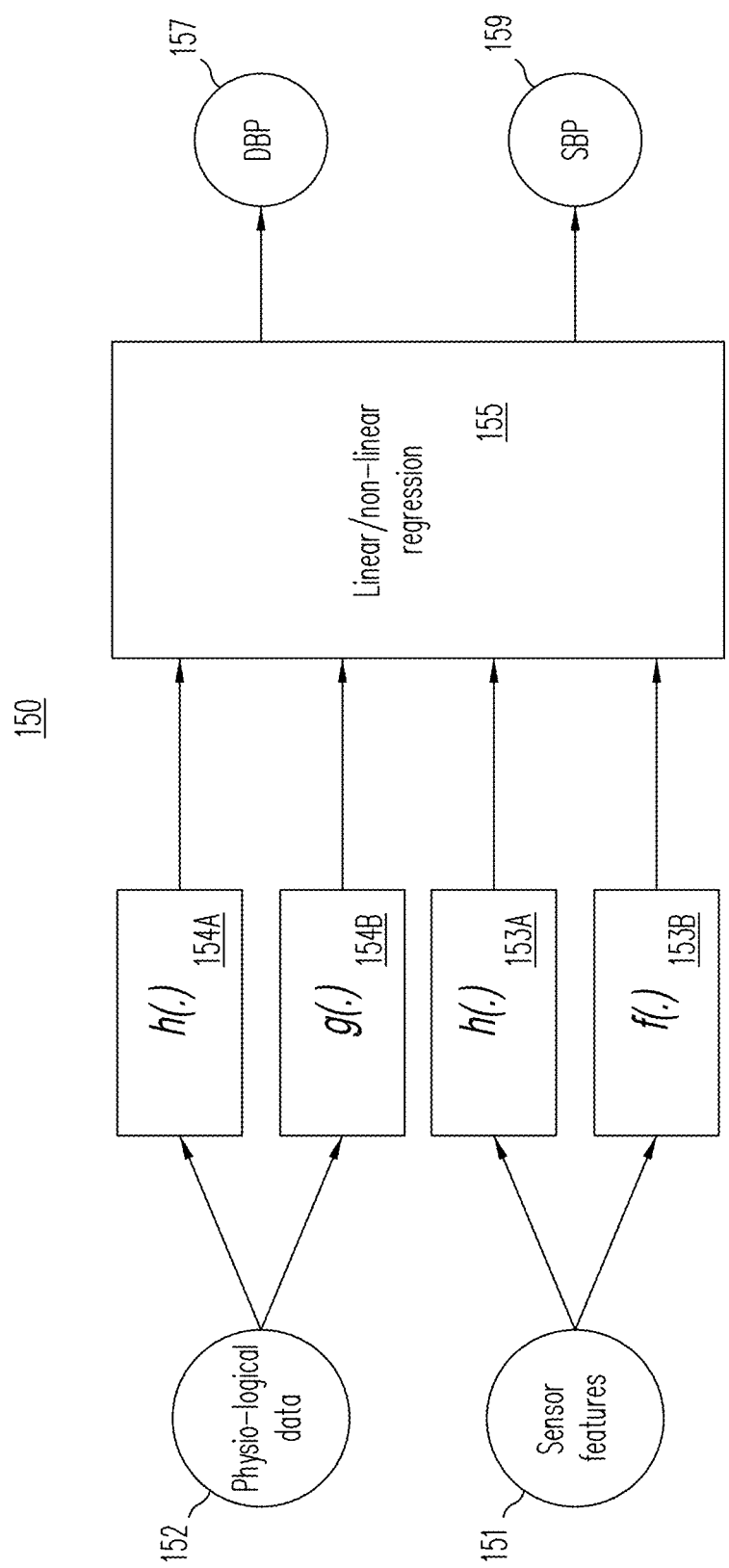
FIG. 1D is a functional block diagram of an embodiment of the invention illustrating an exemplary method of biophysically-informed nonlinear blood pressure regression by signal processing.

Referring now to FIG. 1C, a functional block diagram of a first stage 100 of a signal processing system is shown. FIG. 1D illustrates a functional block diagram of the second stage 150 of the signal processing system, a regression modeling process that functions as a blood pressure predictor to predict systolic blood pressure and diastolic blood pressure. The first stage 100 and the second stage 150 are executed by a signal processor 52 with instructions that may be stored in a storage device 54,56.

A vital signs scanner (such as vital signs scanner 102 shown in FIGS. 9A-9B) concurrently captures ECG and PPG signals with its ECG and PPG sensors. The ECG and PPG signals from the capturing system are signals that are coupled into the first stage 100 of the signal processing system that is coupled together as shown in FIG. 1C.

The first stage 100 receives ECG and PPG signals from ECG and PPG sensors and extracts features from the waveforms of the ECG and PPG signals. Accordingly, the first stage 100 of signal processing system may be referred to as a sensor feature extraction stage or signal processing stage for the ECG and PPG signals. The first stage 100 can generate the signal outputs of ECG spectral scope, ECG spread, pulse wave transit time (PWTT), pulse rate, PPG wave-shape, and PPG spectral slope from sensor data.

During sensor feature extraction by the first stage 100, the raw ECG signal from the ECG sensor is coupled into a Finite Impulse Response (FIR) filter 101 with appropriate cutoff frequencies. The FIR filter 101 may be implemented as either a zero-delay forward-backward convolution. This FIR filter 101 pre-conditions the raw ECG signal, by, for example, removing drift due to very low frequency artifacts.

The filtered ECG signal output from the FIR filter 101 is coupled into a normalizer 102 to undergo a normalization process. The normalizer 102 and normalizing process re-scales the amplitudes of the filtered ECG output to a known numerical range (e.g., range between 0 and 1) to generate a normalized filtered ECG signal. The normalized filtered ECG signal is coupled into an L1 trend filter 103, a linear prediction analyzer (LPA) 120, and a statistics generator/analyzer 118.

Statistical spread values (e.g., standard deviation, absolute deviation) for the ECG signal are calculated by the statistics generator/analyzer 118 from the normalized ECG output signal. The statistical spread values for the ECG signal are referred to herein as the ECG spread.

A linear prediction analysis is performed by the linear prediction analyzer (LPA) 117 on the normalized ECG signal output from the normalizer 102. The linear prediction analysis process performed by the LPA 117 generates and outputs an ECG spectral slope feature.

The normalized filtered ECG signal is also coupled into a nonlinear trend filter 103, such as an L1 trend filter by Seung-Jean Kim et al. for example. The nonlinear trend filter 103 removes white noise and all other signal details except the main cardiac events known as the QRS complex to generate a QRS ECG signal.

Figure 7A:
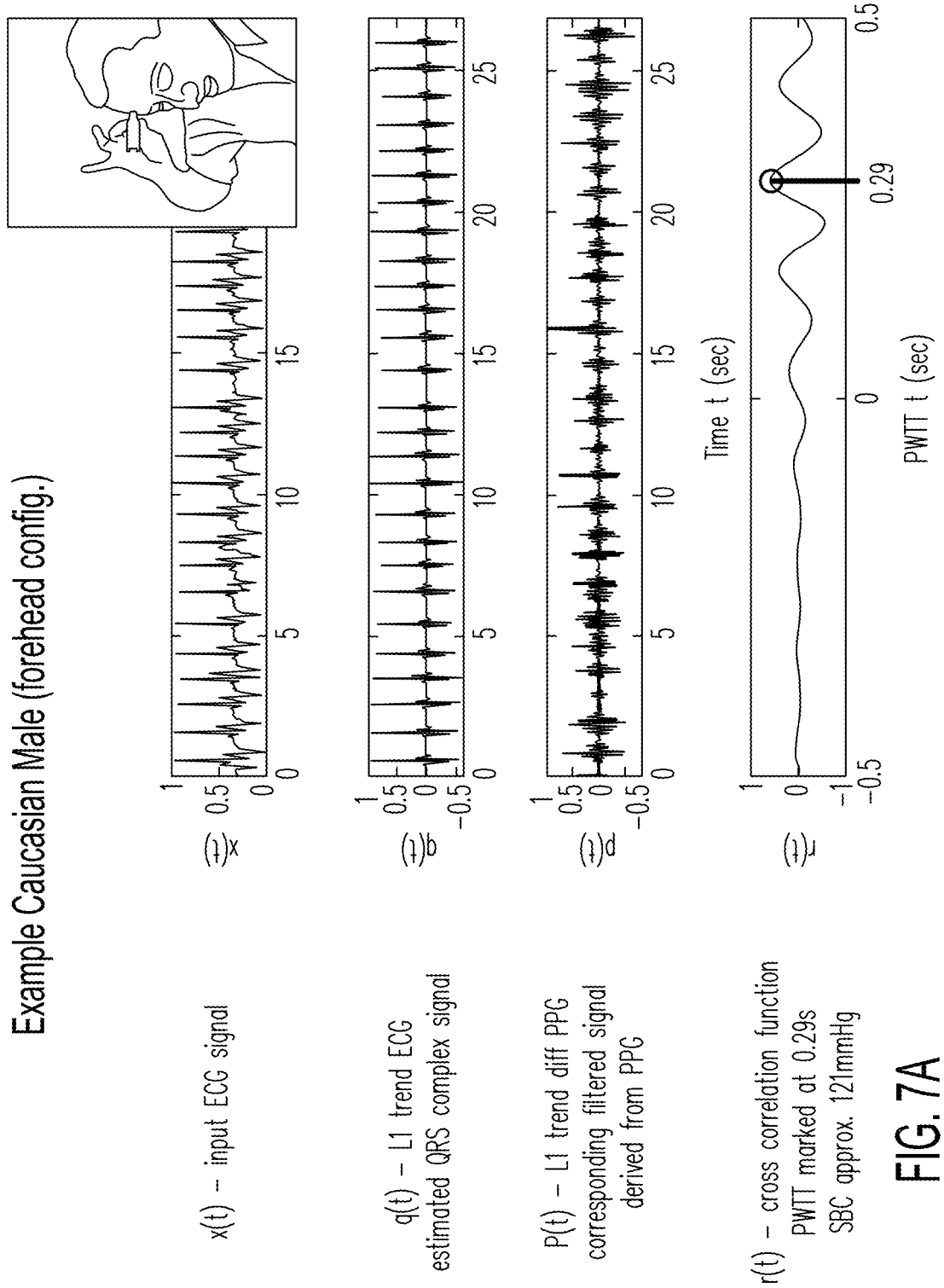
FIG. 7A illustrates exemplary graphs of waveform signals including an exemplary ECG waveform for a Caucasian male.
Figure 7B:
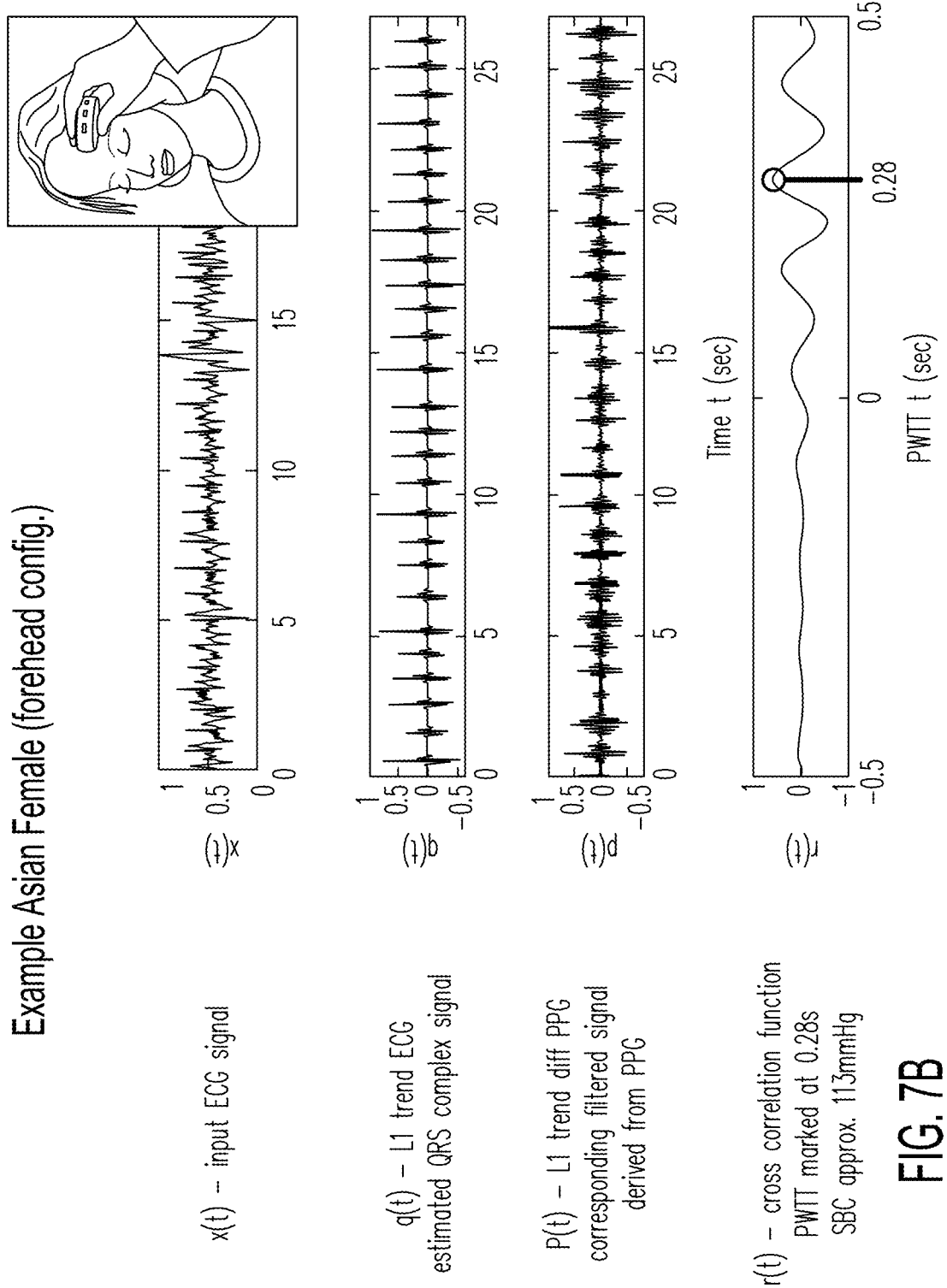
FIG. 7B illustrates exemplary graphs of waveform signals including an exemplary ECG waveform for an Asian female.
Figure 8A:
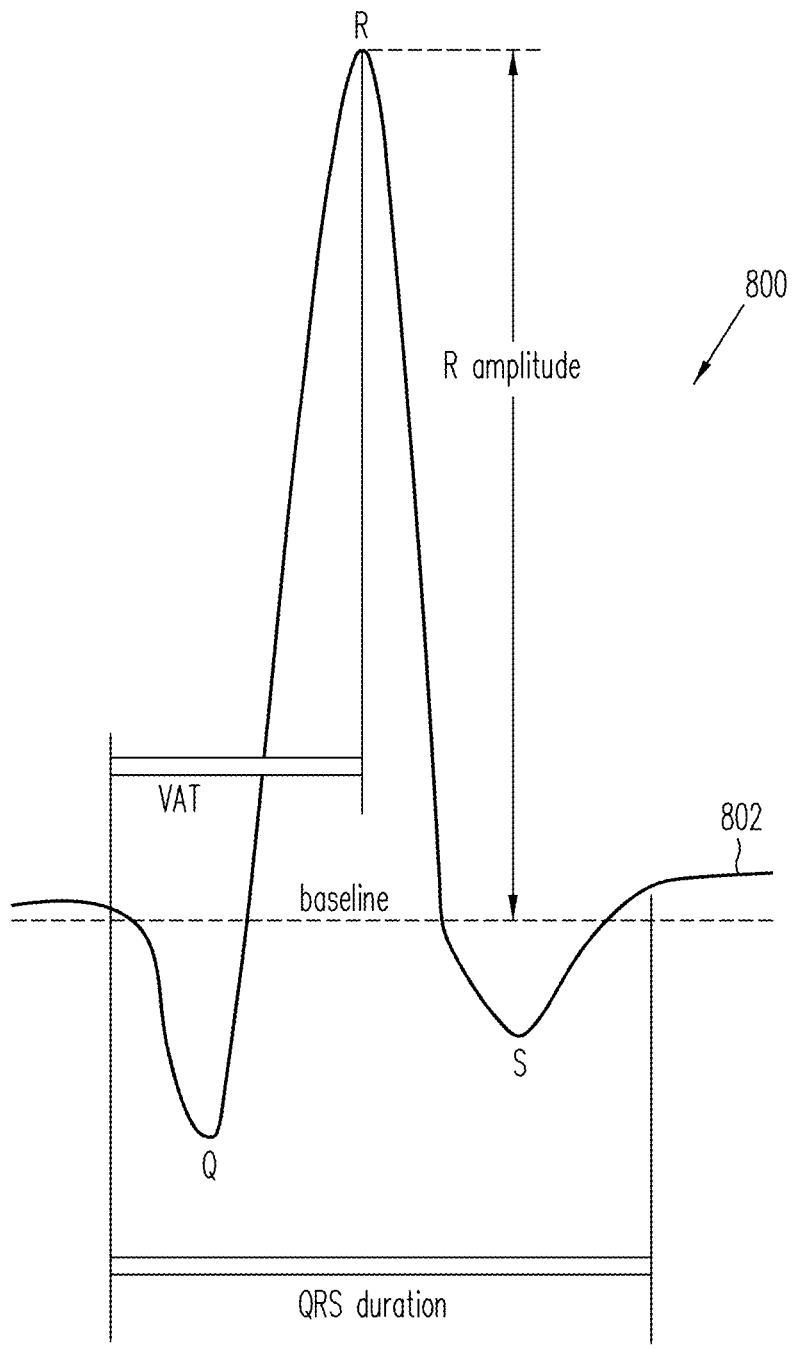
FIG. 8A shows a single exemplary QRS complex in an ECG waveform.
Figure 8B:
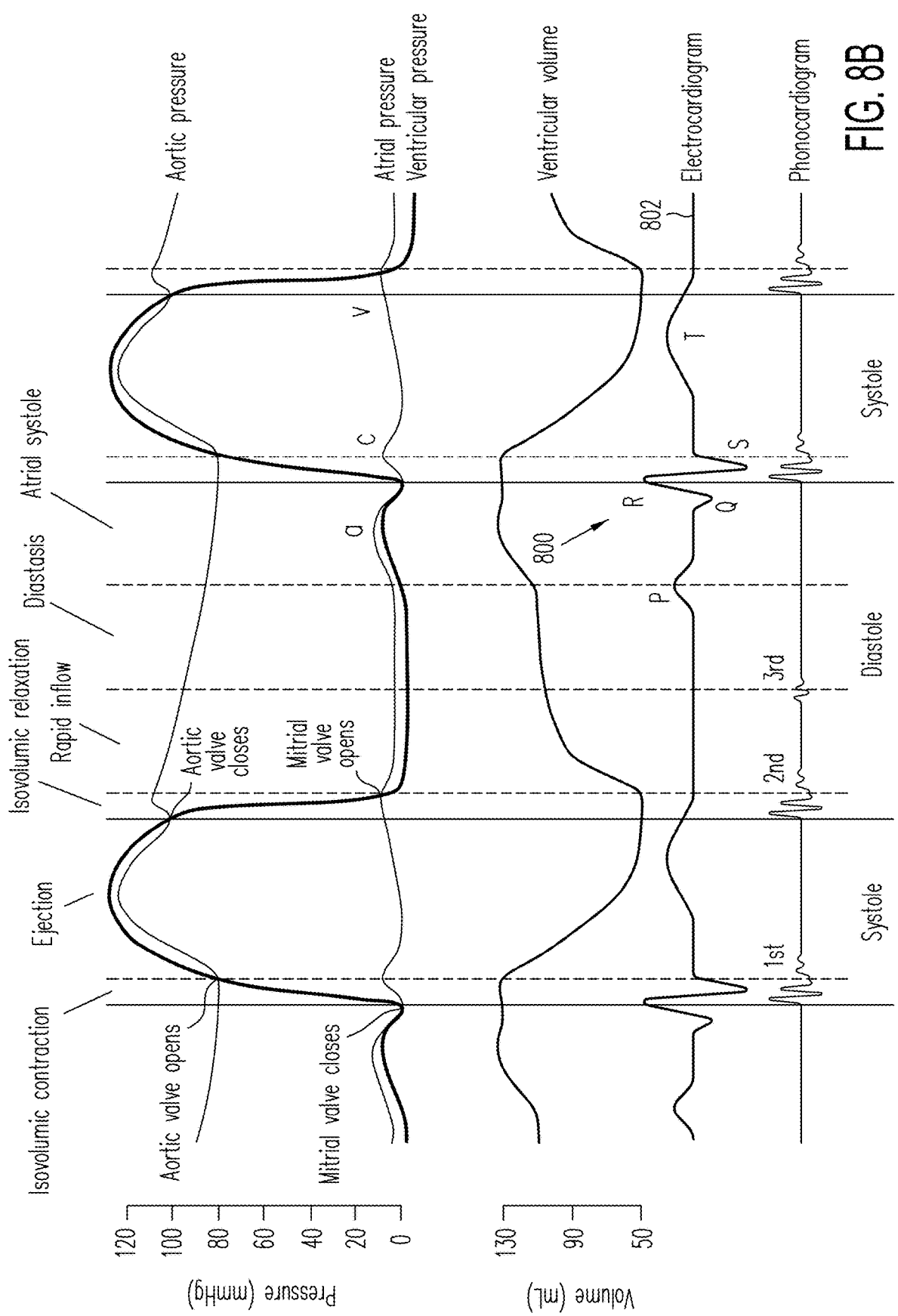
FIG. 8B shows how the exemplary QRS complex in an ECG waveform relates to blood pressure and the function of a human heart.

A QRS complex is the combination of three of the graphical deflections seen on a typical electrocardiogram (ECG). FIG. 8A illustrates a schematic diagram of a single QRS complex 800 in an ECG signal waveform. FIGS. 7A-7B illustrate a waveform q(t) having a sequence of QRS complexes estimated from the input ECG signal x(t). FIG. 8B shows how the exemplary QRS complex 800 in an ECG waveform 802 relates to blood pressure and the function of a human heart.

The QRS ECG signal from the nonlinear trend filter 103 is coupled into a normalizer 103A. The QRS ECG signal is normalized by the normalizer 103A to an amplitude of known range (e.g., range between 0 and 1) to generate a normalized QRS ECG signal.

The normalized QRS ECG signal is then coupled into a fast Fourier transformer (FFT) 103B to undergo a fast Fourier transform process. The fast Fourier transform process on the normalized QRS ECG signal generates an output result (referred to as transformed QRS ECG signal) in the frequency domain to indicate its spectral frequency components. The transformed QRS ECG signal generated by FFT 103B is coupled into a cross correlator 104 to undergo a cross correlation process over a maximum time window Tmax 104A. The maximum time window value Tmax 104A may be set to one half the sampling rate and entered into the cross-correlator 104.

In parallel with the ECG signal, the PPG signal that is concurrently captured is coupled into an FIR filter 111 as shown in FIG. 1C. The FIR filter 111 is similar to the FIR filter 101 with cutoff frequencies that a appropriated to the PPG signal. The FIR filter 111 may be implemented as either a zero-delay forward-backward convolution. The FIR filter 111 pre-conditions the raw PPG signal, by, for example, removing drift due to very low frequency artifacts.

The filtered PPG output signal is coupled into a normalizer 112. The normalizer 112 performs a signal normalizing process that re-scales the amplitudes of the filtered PPG signal to a known numerical range (e.g., between 0 and 1) to generate a normalized PPG signal. The normalized PPG signal is coupled from the normalizer 112 into a differentiator 113, a harmonic analyzer 116, and a linear prediction analyzer (LPA) 117.

A harmonic analysis is performed by the harmonic analyzer 116 on the normalized PPG signal output from the normalizer 112 in response to the pulse rate output. Harmonic ratios of the pulse rate are used by the harmonic analyzer 116 to estimate several PPG wave-shape features regarding the power spectral density of the PPG signal, namely its five first harmonics.

A linear prediction analysis is performed by a linear prediction analyzer (LPA) 117 on the normalized PPG signal. The linear prediction analysis performed by the LPA 117 generates the PPG spectral slope feature.

To determine pulse rate and PWTT features, the normalized PPG signal is digitally differentiated by a differentiator 113 to estimate the blood flow rate. The differentiator 113 estimates the blood flow rate signal by performing a first order gradient on the normalized PPG signal. The resultant flow-rate signal is coupled into a nonlinear trend filter 114.

The nonlinear trend filter 114 removes all high-frequency noise in the blood flow-rate signal, retaining a main cardiac impulse. The main cardiac impulse signal generated by the nonlinear trend filter 114 is then coupled into the normalizer 114A.

The normalizer 114A performs a signal normalizing process that re-scales the amplitudes of the main cardiac impulse signal down to a known numerical range (e.g., between 0 and 1) to generate a normalized cardiac impulse signal. The normalized cardiac impulse signal is then coupled from the normalizer 114A into a fast Fourier transformer (FFT) 114B.

The fast Fourier transform process performed by the FFT 114B on the normalized cardiac impulse signal generates an output result (referred to as transformed cardiac impulse signal) in the frequency domain or space to indicate its spectral frequency components. The transformed cardiac impulse signal generated by FFT 114B is coupled into the cross correlator 104 to undergo a cross correlation process with the transformed ECG QRS complex signal from the FFT 103B. The transformed cardiac impulse signal generated by FFT 114B is also coupled into the auto-correlator 115 to undergo an auto-correlation process of the PPG related signal.

Figure 10A:
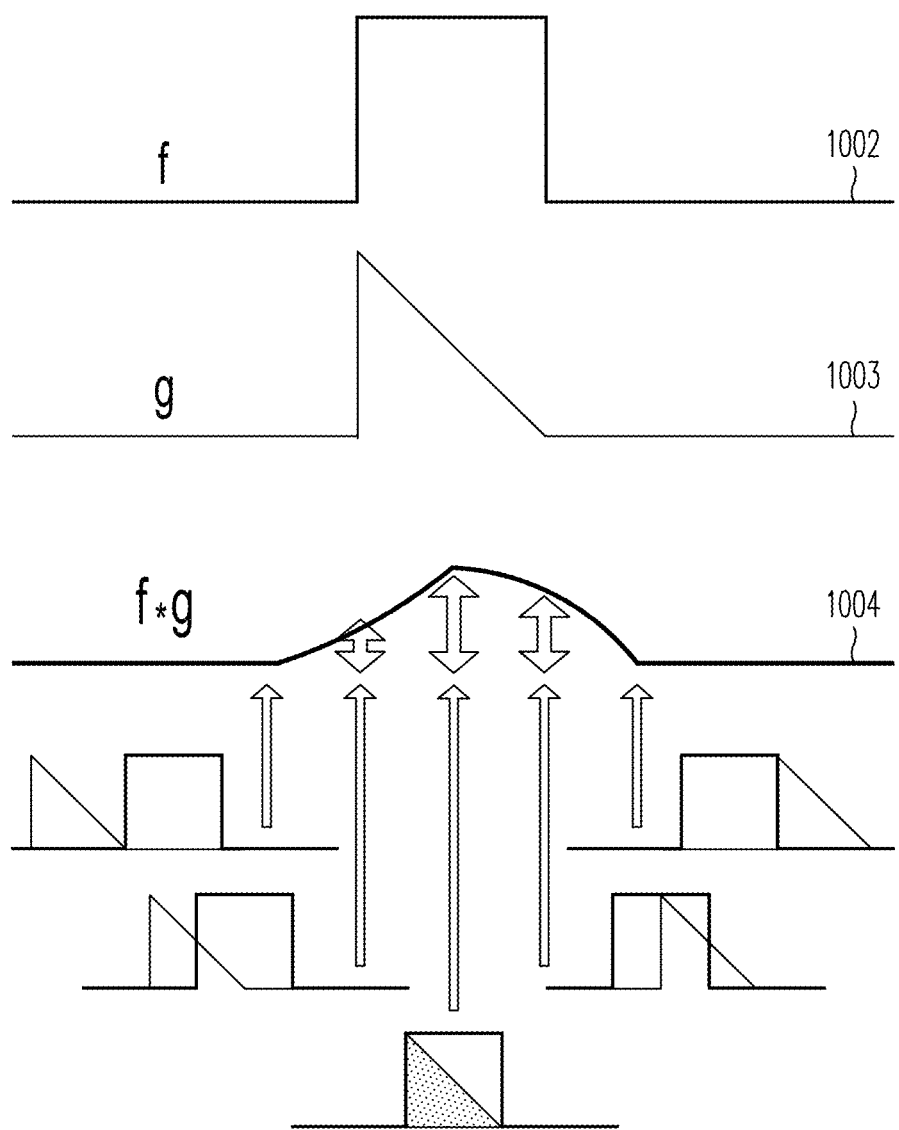
FIG. 10A graphically illustrates cross-correlation between two exemplary signals.

A cross-correlation between two waveform signals is a measure of similarity of two waveforms as a function of a time-lag applied to one of them. An example of cross correlation between two signals is shown by FIG. 10A.

The transformed cardiac impulse signal generated from the PPG signal is cross-correlated against the transformed ECG QRS complex signal by the cross-correlator 104 to estimate the pulse wave transit time (PWTT) feature. A maximum time window value Tmax 104A is set to one half of the sampling rate and enter into the cross correlator 104 and the cross-correlation process to define the length or size of its correlation window.

The detection of a maximum peak in the cross-correlated output signal provides an accurate value of the pulse wave transit time (PWTT) feature. The cross-correlation output signal is coupled into a maximum peak detector 125.

The maximum peak detector 125 determines the maximum peak in the cross-correlation output signal to generate the PWTT feature output from the ECG and PPG signals. The maximum peak detector 125 may use an inverse fast Fourier transform (IFFT) convolution on the cross-correlation output signal to determine the maximum peak therein.

Figure 10B:
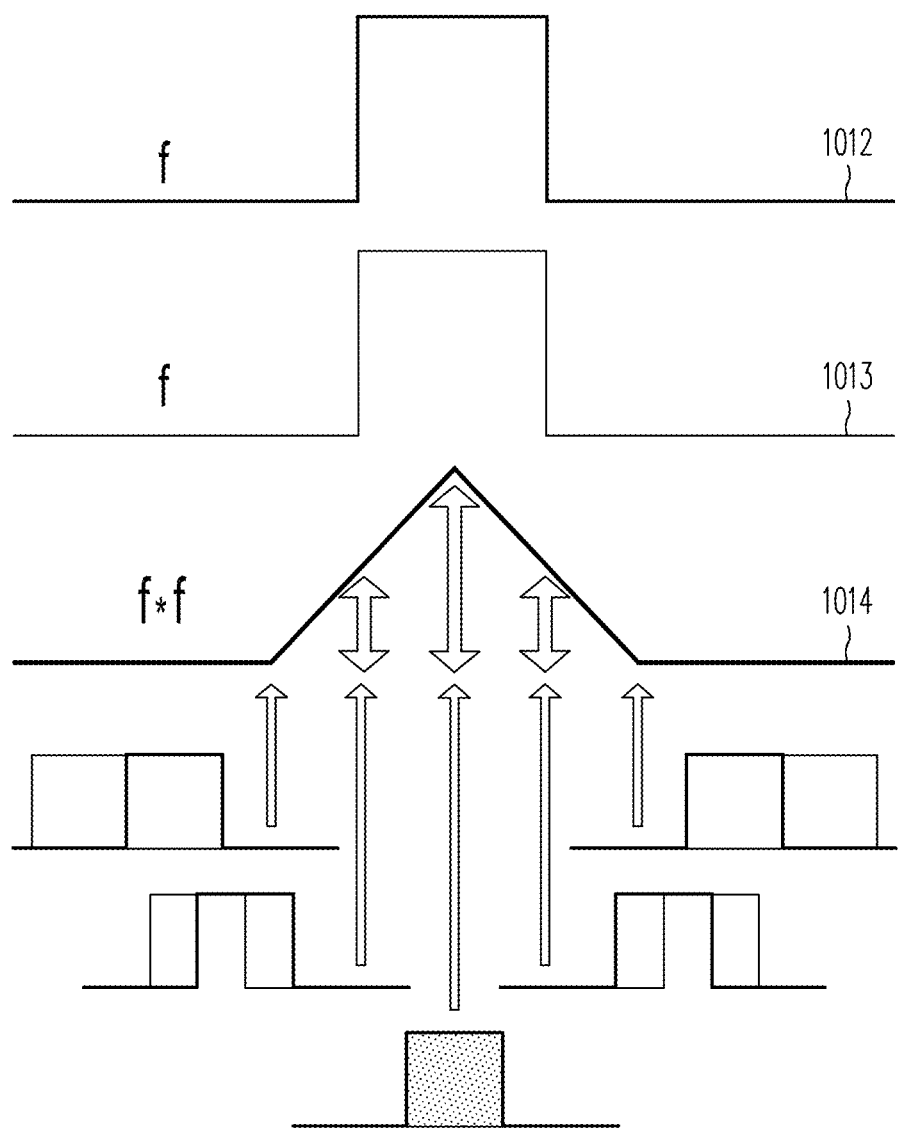
FIG. 10B graphically illustrates auto-correlation of an exemplary signal.

The transformed ECG QRS complex signal is further auto-correlated by the auto-correlator 115. A maximum time window value Tmax 115A is set to twice the sampling rate and entered into the auto-correlator 115. The auto-correlation process defines the length or size of its correlation window. An autocorrelation of a signal is a cross-correlation of the signal with itself, such as shown by FIG. 10B for example. In FIG. 10B, waveforms show the autocorrelation process between an f signal waveform 1012 and itself to form the resultant auto-correlation waveform 1014. In an autocorrelation of a signal, there is usually a peak at a lag of zero. A maximum peak in the autocorrelation output signal is used to estimate the pulse rate feature. The autocorrelation output signal is coupled into a maximum peak detector 126.

The maximum peak detector 126 determines the maximum peak in the autocorrelation output signal to generate the pulse rate feature output in the PPG signal. The maximum peak detector may use an inverse fast Fourier transform (IFFT) convolution on the autocorrelation output signal to determine the maximum peak therein.

Regression Modeling and Blood Pressure Predictor

Figures 1, 6A:
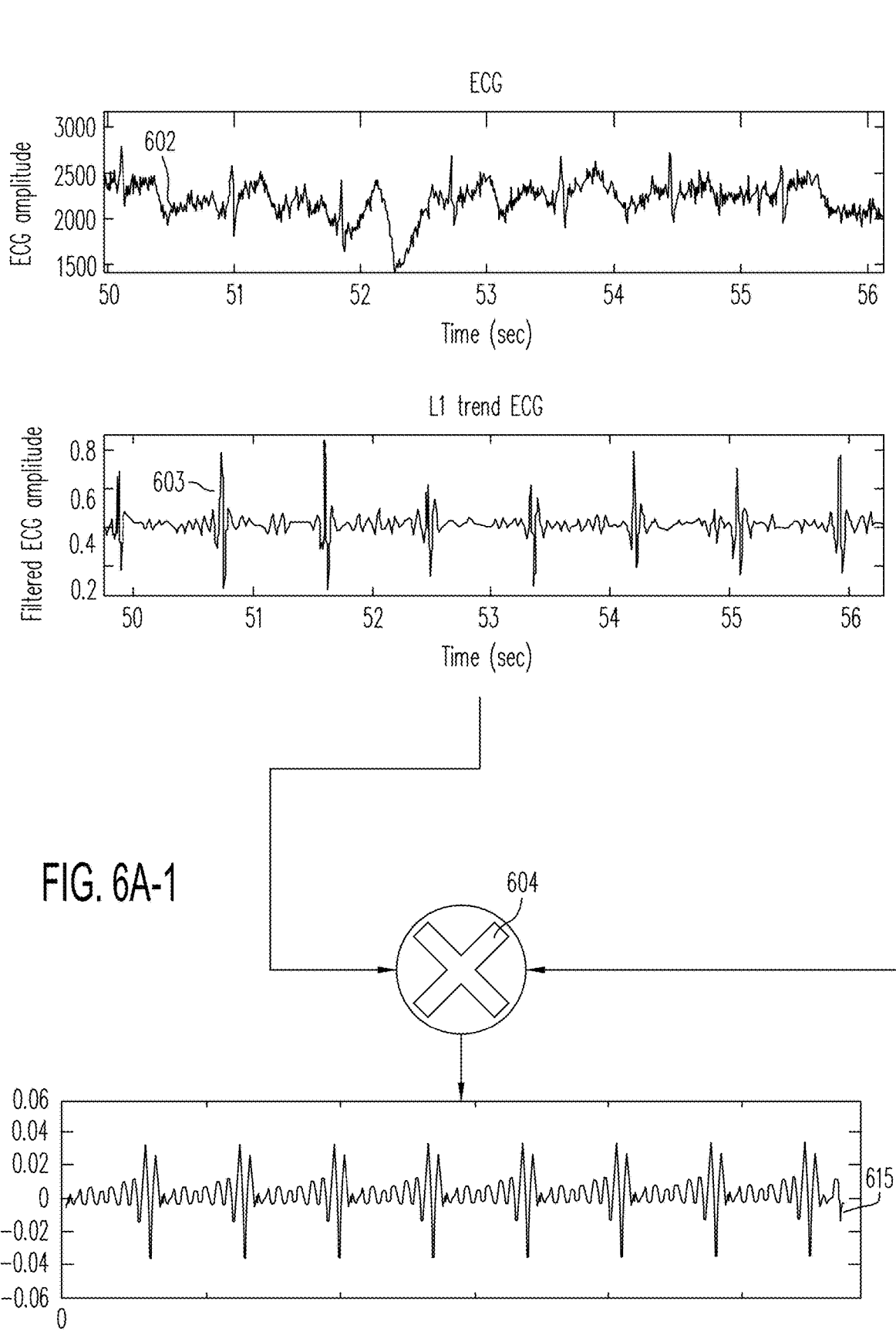
FIG. 6A (6A-1 and 6A-2) and FIG. 6B illustrate a plurality of graphs and signals to illustrate how the cross-correlation algorithm of the embodiments of the invention increase the precision of determining blood pressure with a cross-correlation algorithm.
Figure 6A:
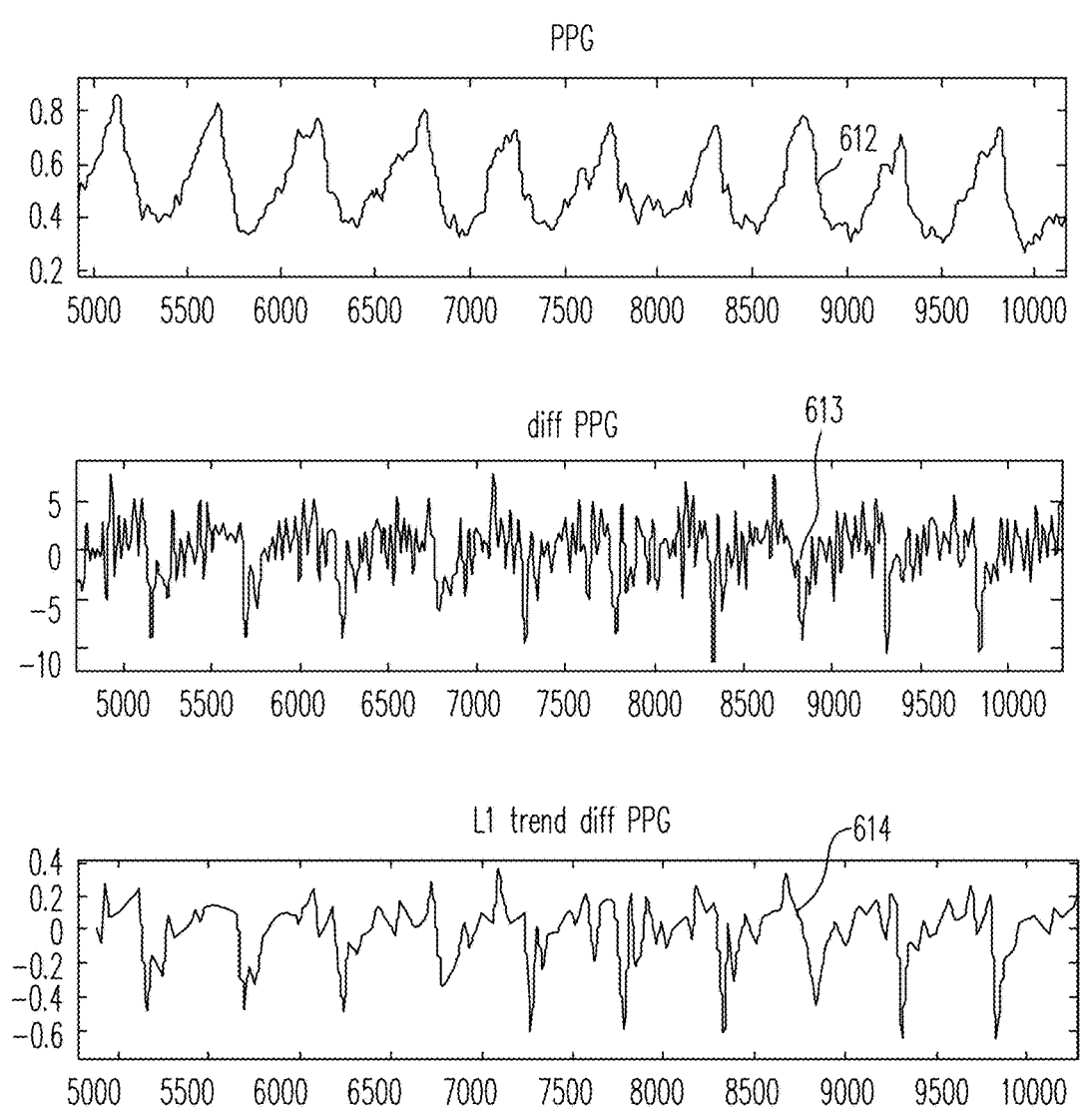
Figure 6A:
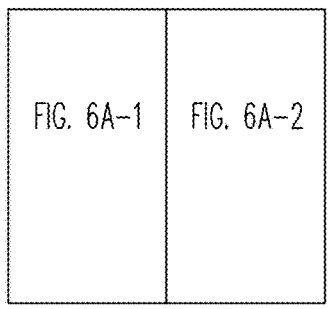

Referring now to FIG. 1D, an illustration of the second stage 150 of the signal processing system is shown for the calculation/prediction of systolic and diastolic blood pressure (SBP and DBP respectively). Based on sensor features 151, heart rate, PWTT, Pulse Rate, PPG wave shape, PPG spec. slope, PPG spread, extracted as depicted in FIG. 1, and additional physiological data 152 about the user, systolic blood pressure (SBP) 159 and diastolic blood pressure (DBP) 157 can be computed.

Physiological data 152, such as age, weight, height and gender are coupled into one or more nonlinear transformation functions h,g,f 154A-154B. Similar nonlinear transformations h,g,f 153A-153B may be applied to the sensor features 151 extracted from the PPG and ECG signals.

The nonlinear transformation functions 154A-154B and 153A-153B that may be used include functions such as the natural logarithm ln x, or $$\frac{1}{x}$$

or other power transformations such as $$\frac{1}{x^2}.$$

These nonlinear transformations h,g,f 154A-154B and 153A-153B are informed by models of blood flow in the circulatory system (such as the Moens-Korteweg equation which expresses the pressure P as a function of the square of PWTT: P∝f (PWTT$^2$), and the Bernoulli principle which expresses the pressure as a function $$P \propto \frac{a}{PWTT^2} + b).$$

The output of the non-linear transformations h,g,f 154A-154B and 153A-153B are then coupled input to a linear or nonlinear regressor 155.

The linear or nonlinear regressor 155 uses a linear regression method, a nonlinear regression method, or a quasi linear regression method to map the non-linear transformed data into a predicted systolic blood pressure (SBP) 159 and a predicted diastolic blood pressure (DBP) 157. Overall, the transformations h,g,f 154A-154B and 153A-153B and the regressor 155 form a blood pressure model of the modeling process 12 that is used to generate the predicted systolic blood pressure (SBP) 159 and the predicted diastolic blood pressure (DBP) 157.

Biophysical modeling principles, if they are to be simple enough that they can be understood and manipulated in practice and applied under controlled conditions. However, in the field where the principles may be applied, there are many unknown, confounding factors such as physiological parameters, sensor parameters, noise etc. As such, direct biophysical models do not work in practice, however their fundamental physical principles remain valid.

For example, the Moens-Korteweg equation expresses that the pressure P is a function of the square of PWTT by the equation:

$$P \propto h(PWTT^2).$$

The Bernoulli principle, for example, simply expresses conservation of energy in a fluid, so that the pressure is proportional to the inverse of PWTT squared by the equation:

$$P \propto \frac{a}{PWTT^2} + b.$$

The embodiments of the invention exploits some of these biophysically-informed nonlinear equations and principles by injecting them back into the blood pressure model in the form of nonlinear transformations h,g,f 154A-154B and 153A-153B, as described herein.

Physiological data inputs 202 may include subject age, approximate weight, height and gender. For a given user, the parameters of the model of the second stage 150 of the signal processing system to predict systolic blood pressure (SBP) 159 and diastolic blood pressure (DBP) 157 are estimated from training data associating the input data from the user with a set of gold-standard, cuff-based measurements from the user. Once trained and parameters estimated for a given user of the vital signs scanner 902 shown in FIG. 9A-9B, no further training may need to be made.

Figure 12:
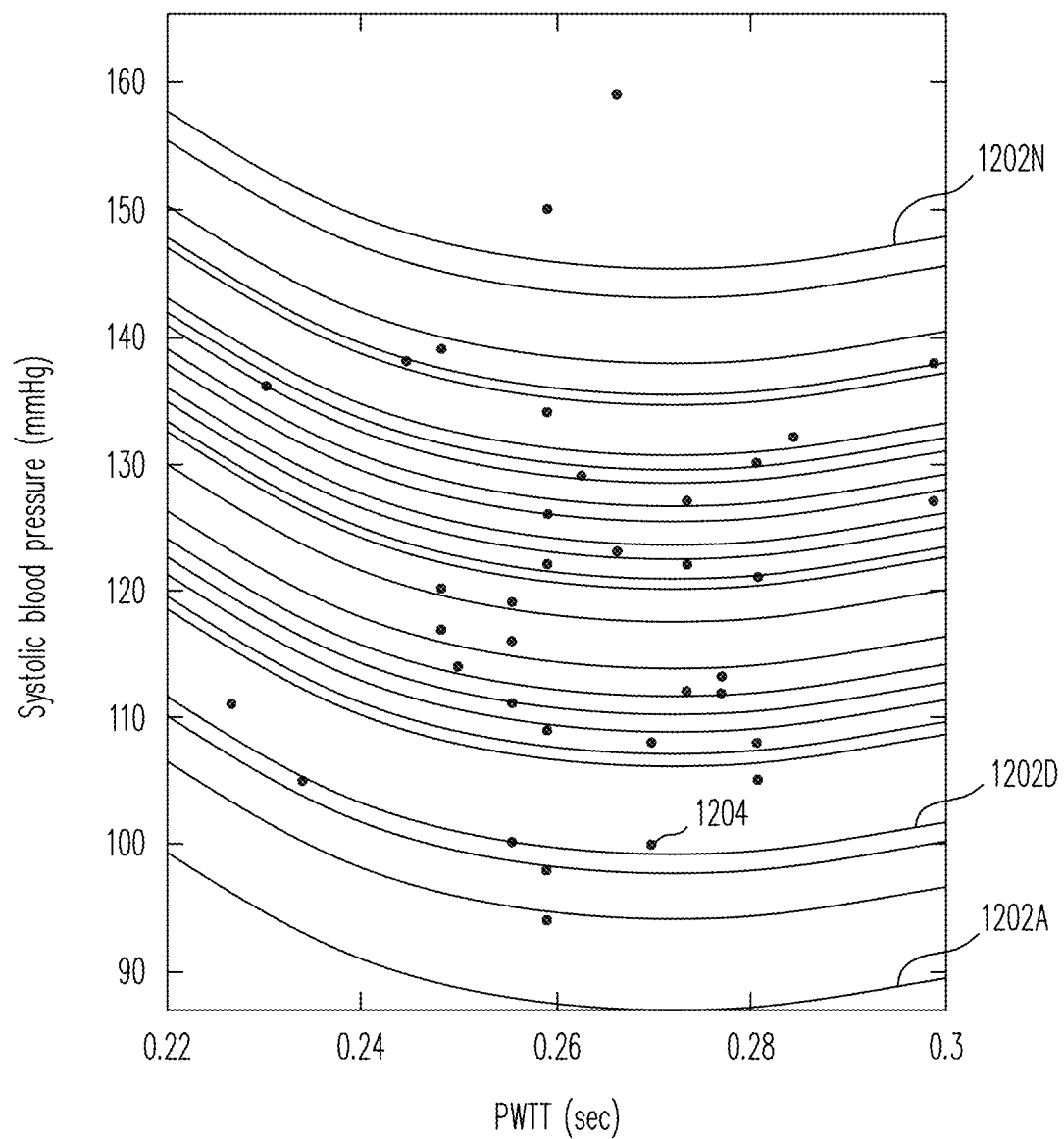
FIG. 12 illustrates an exemplary regression of PWTT to determine systolic blood pressure.

FIG. 12 illustrates an example of regression of PWTT that may be used by the blood pressure model to determine a component of systolic blood pressure (mmHg). The plotted curves 1202A-1202N indicate individualized relationships for different users after training of the model. The points, such as point 1204, on the curves 1202A-1202N illustrate individual predictions. A DBP regression can be similarly formed but with lower BP values. If all other things are unchanged, increasing PWTT generally predicts lowered SBP up to a point.

Figure 13:
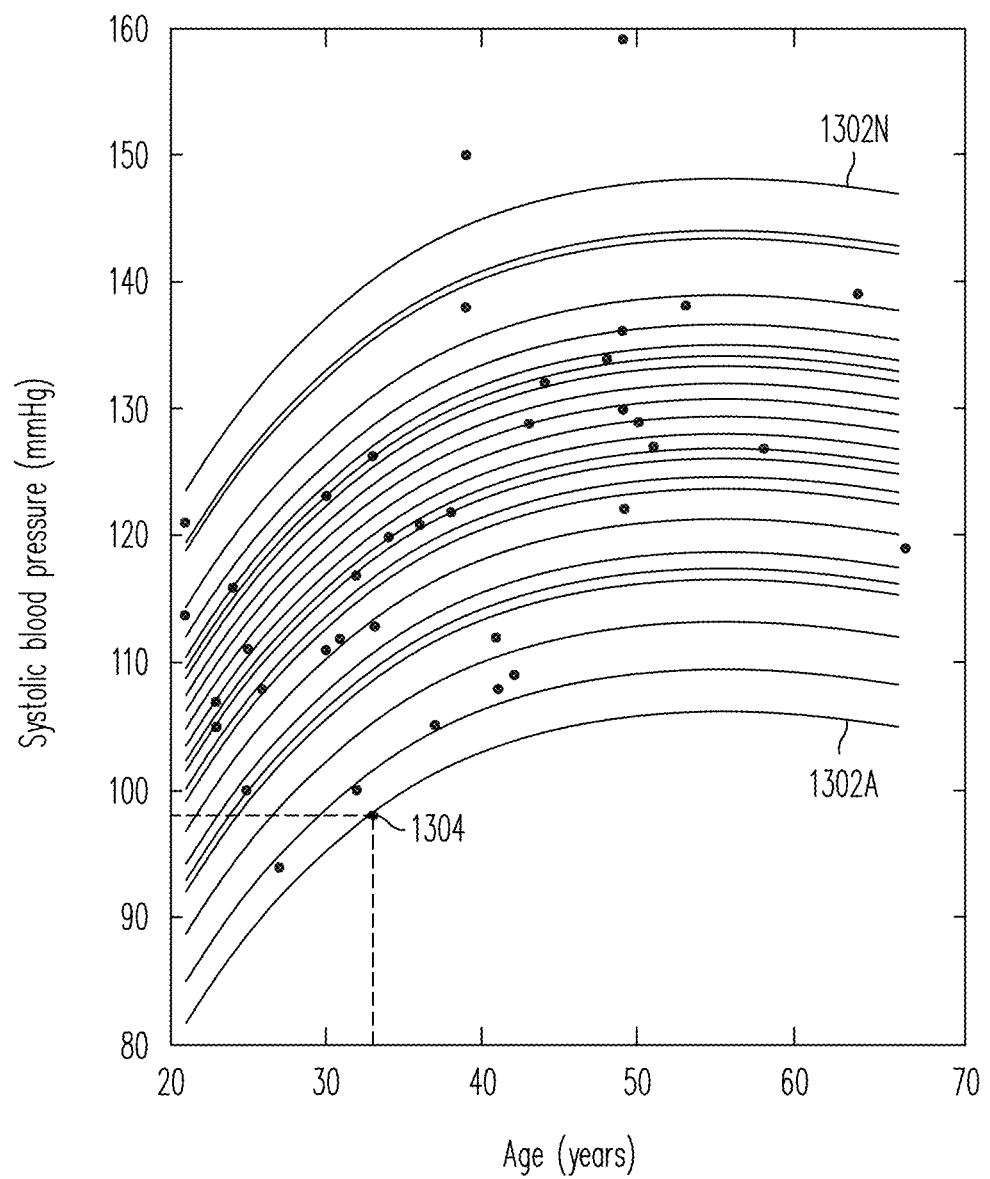
FIG. 13 illustrates an exemplary regression of age in years to determine systolic blood pressure.

FIG. 13 illustrates an example of a regression of age in years that may be used by the blood pressure model to determine another component of systolic blood pressure (mmHg). The plotted curve 1302A-1302N indicate individualized relationships for different users after training of the model. The points, such as point 1304, on the curves 1302A-1302N illustrate individual predictions for different users. A DBP regression is similarly formed but with lower BP values. If all other things are unchanged, increasing age generally predicts increasing SBP up to a point. The regression illustrates an age related loss of vessel-wall elasticity, atherosclerosis, etc.

Using Predictive Algorithms

A PWTT blood pressure measuring device that uses sensory data alone requires at least a first calibration with an external blood pressure cuff of a blood pressure measuring device. Once the first calibration is done, the PWTT methods of determining blood pressure can work but it can still drift over time becoming inaccurate. Accordingly, repeated calibrations have been used to reach medical quality results. Extended self-optimizing models can be used to predict systolic and diastolic blood pressures and avoid the repeated calibrations. The book "Elements of Statistical Learning: Data mining, Inference, Prediction", Second edition by Trevor Hastie, Robert Tibshirani, Jerome Friedman and published by Springer generally describes algorithms with self-optimizing models.

Figure 2A:
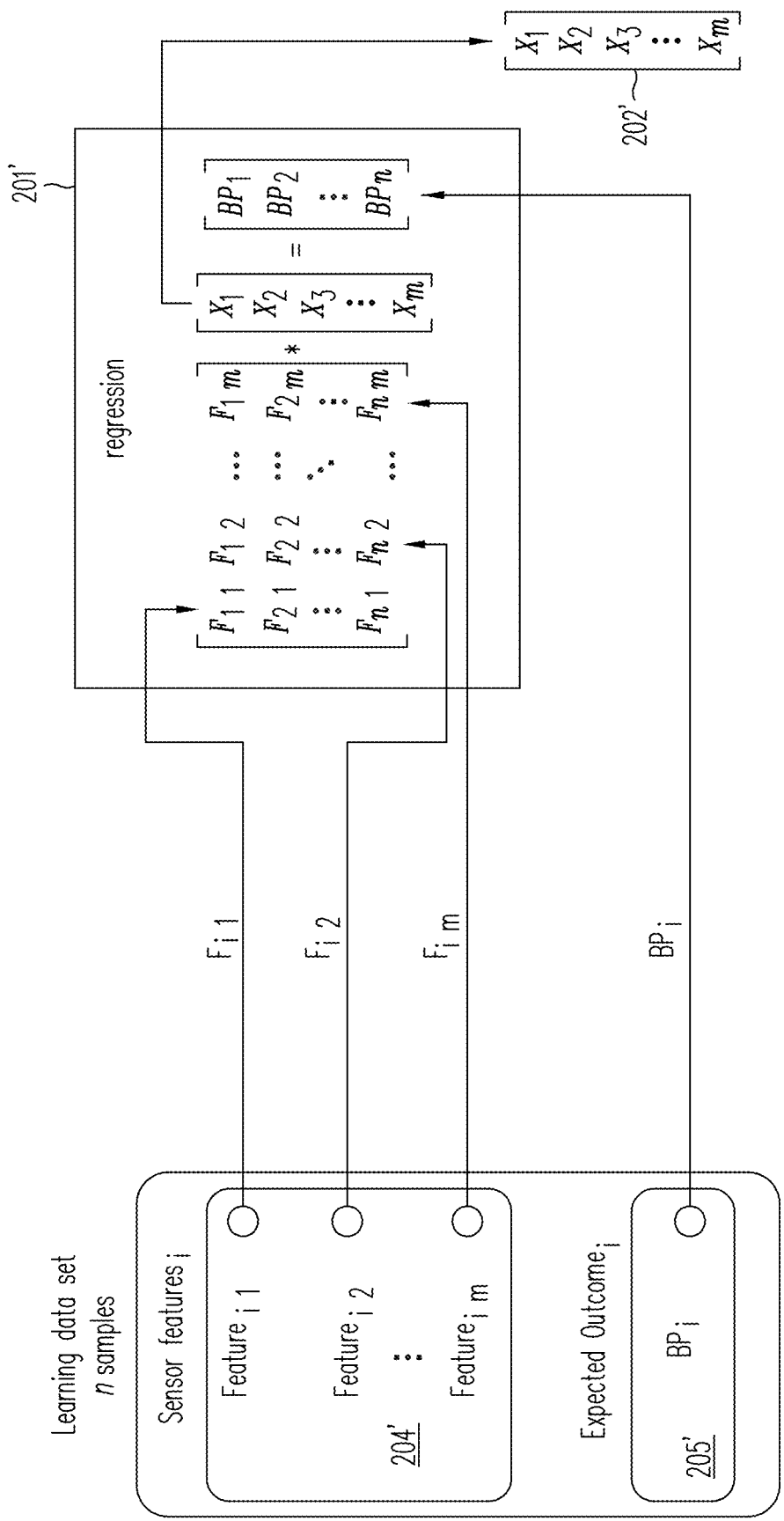
FIG. 2A illustrates a naïve exemplary regression model for a learning phase of the blood pressure predictor without considering physiological data.

Referring now to FIG. 2A, an exemplary naïve learning or training algorithm is illustrated in the context of solving a hypothetical blood pressure BP. During the learning or training phase of the regression algorithm, a set of n examples is provided to the regression algorithm 201'. Each example i of the n examples may be described by a line vector Mi as follows:

$$M_i = [F_{i1}\ F_{i2}\ \ldots\ F_{im}]$$

The vector Mi represents the sensory input (204') to the regression algorithm. During this learning phase, the variable $BP_i$ (205') is recorded along with the measurements for the sensory input. During the learning phase given the measurements for the line vector and the blood pressure BPi, the goal of the linear regression 201' is to find the best estimate for the vector X 202' where the transpose of the vector X is as follows:

$$X^T = [X_1\ X_2\ X_3\ \ldots\ X_m]$$

The vector X solves the matrix equation for blood pressure as follows:

$$\begin{bmatrix} F_{11} & F_{12} & \cdots & F_{1m} \\ F_{21} & F_{22} & \cdots & F_{2m} \\ \vdots & \vdots & \ddots & \vdots \\ F_{n1} & F_{n2} & \cdots & F_{nm} \end{bmatrix} * \begin{bmatrix} X_1 \\ X_2 \\ X_3 \\ \vdots \\ X_m \end{bmatrix} = \begin{bmatrix} BP_1 \\ BP_2 \\ \vdots \\ BP_n \end{bmatrix}$$

In practice, this matrix equation can be solved using MATLAB software with the following instruction:
[X, ~]=regress(M, BP) where M and BP have n lines.

Figure 3A:
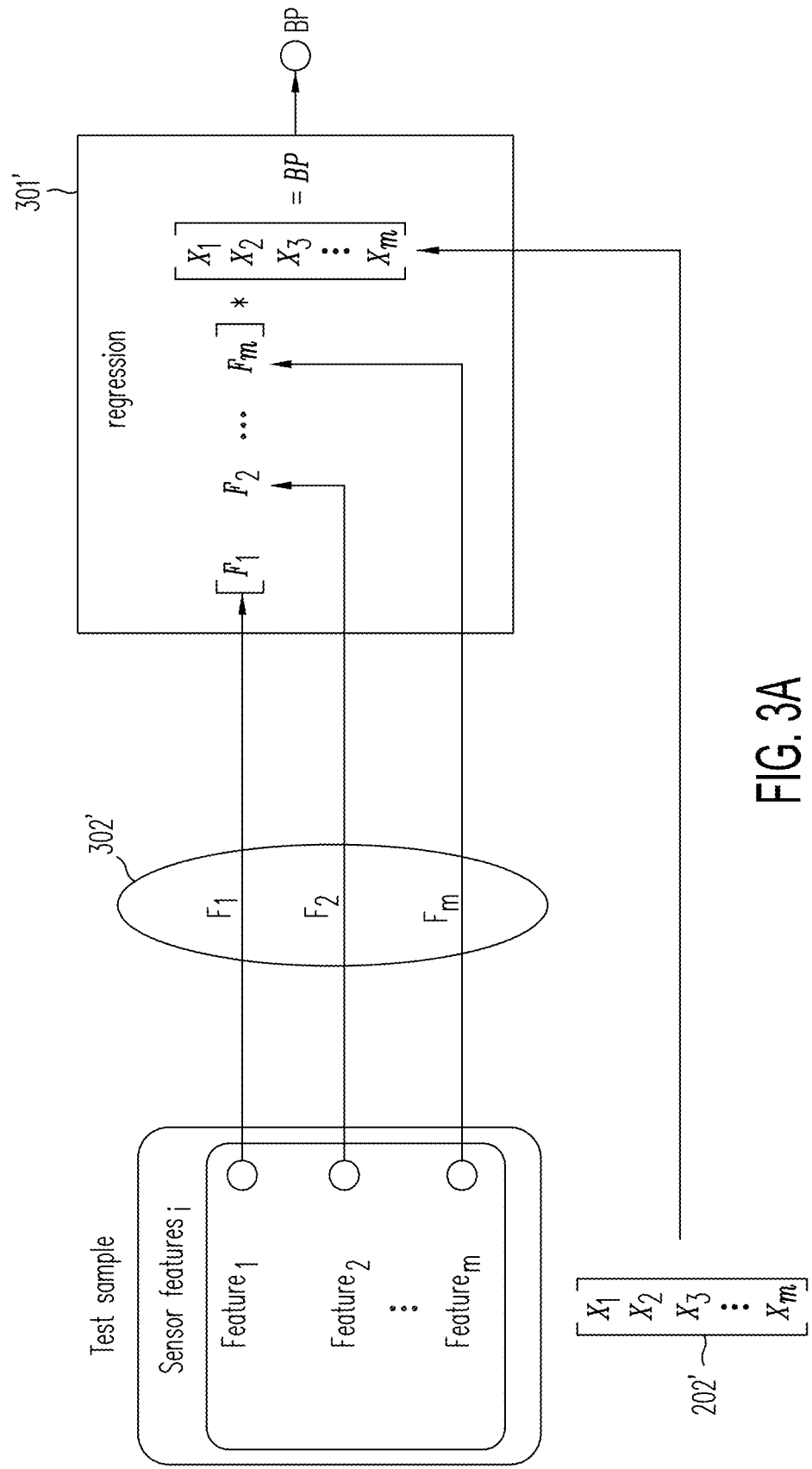
FIG. 3A illustrates a naïve exemplary regression model for a test phase of the blood pressure predictor without considering physiological data.

Referring now to FIG. 3A, a testing process or phase may be used to test accuracy of the matrix of X coefficients. During the testing phase, a measurement 302' is taken of sensory output from the sensors to form the matrix M $$M = [F_1\ F_2\ \ldots\ F_m]$$

The trained X vector 202' from the training process, $X^T = [X_1\ X_2\ X_3\ \ldots\ X_m]$ is then used with the measurement matrix M to calculate the blood pressure with the blood pressure matrix equation $$M * X = BP$$

While mathematical equations for a predictive model for blood pressure have been described using linear regression for simplicity, non-linear regressions algorithms and models can also be used.

Using only sensory features, accurate systolic blood pressure (SBP) prediction and diastolic blood pressure (DBP) prediction from sensor data requires repeated calibration. If other inputs are used, repeated calibration may be avoided.

Using Predictive Algorithms with Physiological Data and Sensor Features

Figure 2B:
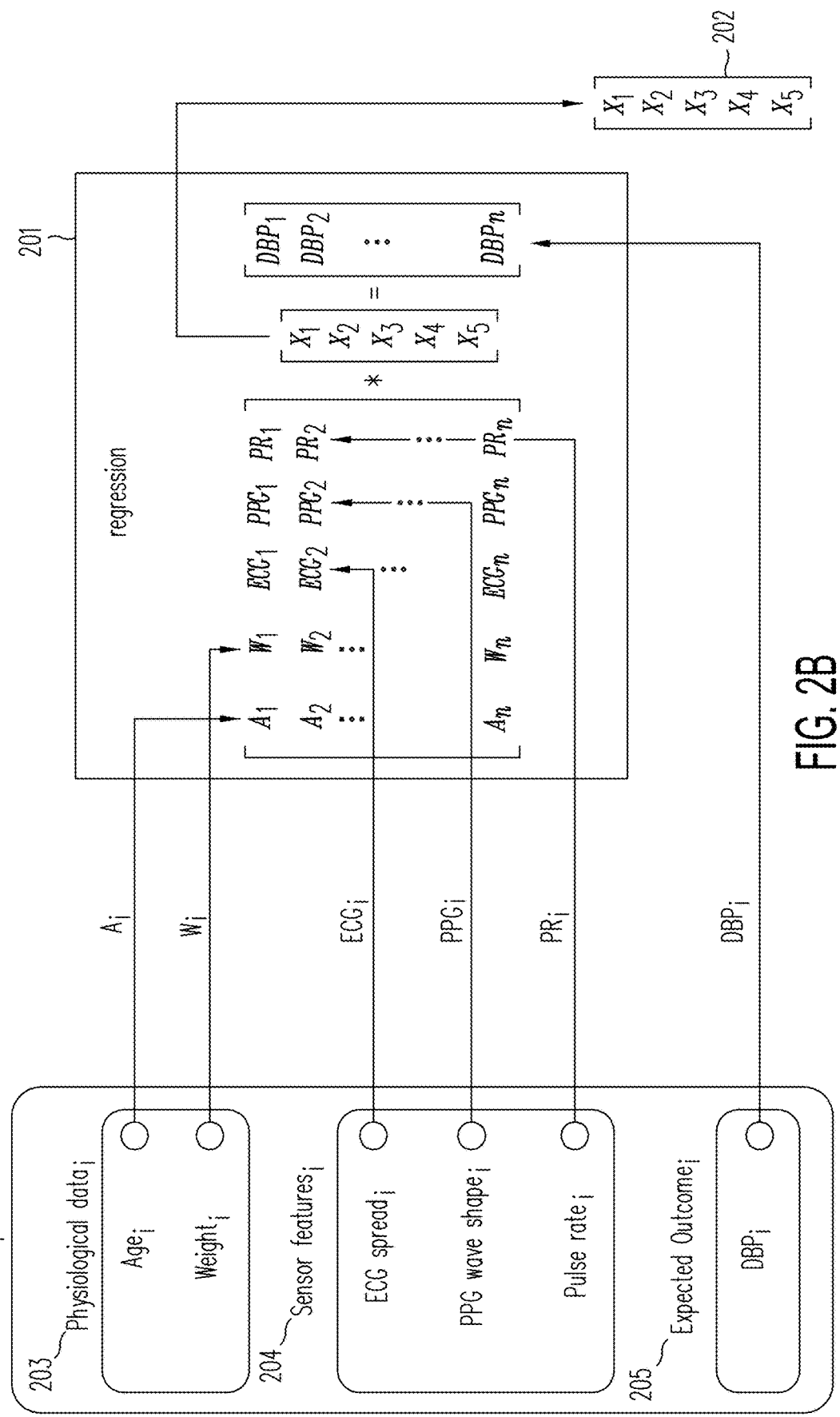
FIG. 2B illustrates a naïve diastolic blood pressure regression model for a learning phase of the blood pressure predictor with physiological data.

Referring now to FIG. 2B, a naïve diastolic blood pressure learning algorithm is described. During the learning phase, a set of n examples is provided to the regression algorithm 201. Each of the examples i is described by a line vector as follows $$[A_i\ W_i\ ECG_i\ PPG_i\ PR_i]$$

representing respectively physiological data (203), e.g., age Ai, weight Wi, and sensor features (204)—ECG spread ECGi, PPG wave shape PPGi, Pulse rate PRi, captured by sensors and signal processed in a measurement. During this learning phase, the diastolic blood pressure $DBP_i$ (205) measurement from a cuff-based blood pressure instrument is recorded along with the measurements for ECG, PPG, and the extracted signal features for each user of a plurality of users.

The goal of the linear regression 201 is to find the best estimate for vector coefficients X 202, solving the equation:

$$\begin{bmatrix} A_1 & W_1 & ECG_1 & PPG_1 & PR_1 \\ A_2 & W_2 & ECG_2 & PPG_2 & PR_2 \\ \vdots & \vdots & \vdots & \vdots & \vdots \\ A_n & W_n & ECG_n & PPG_n & PR_n \end{bmatrix} * \begin{bmatrix} X_1 \\ X_2 \\ X_3 \\ X_4 \\ X_5 \end{bmatrix} = \begin{bmatrix} DBP_1 \\ DBP_2 \\ \vdots \\ DBP_n \end{bmatrix}$$

After the vector coefficients X are solved, the scanners can be used in a test phase to predict diastolic blood pressure.

Figure 3B:
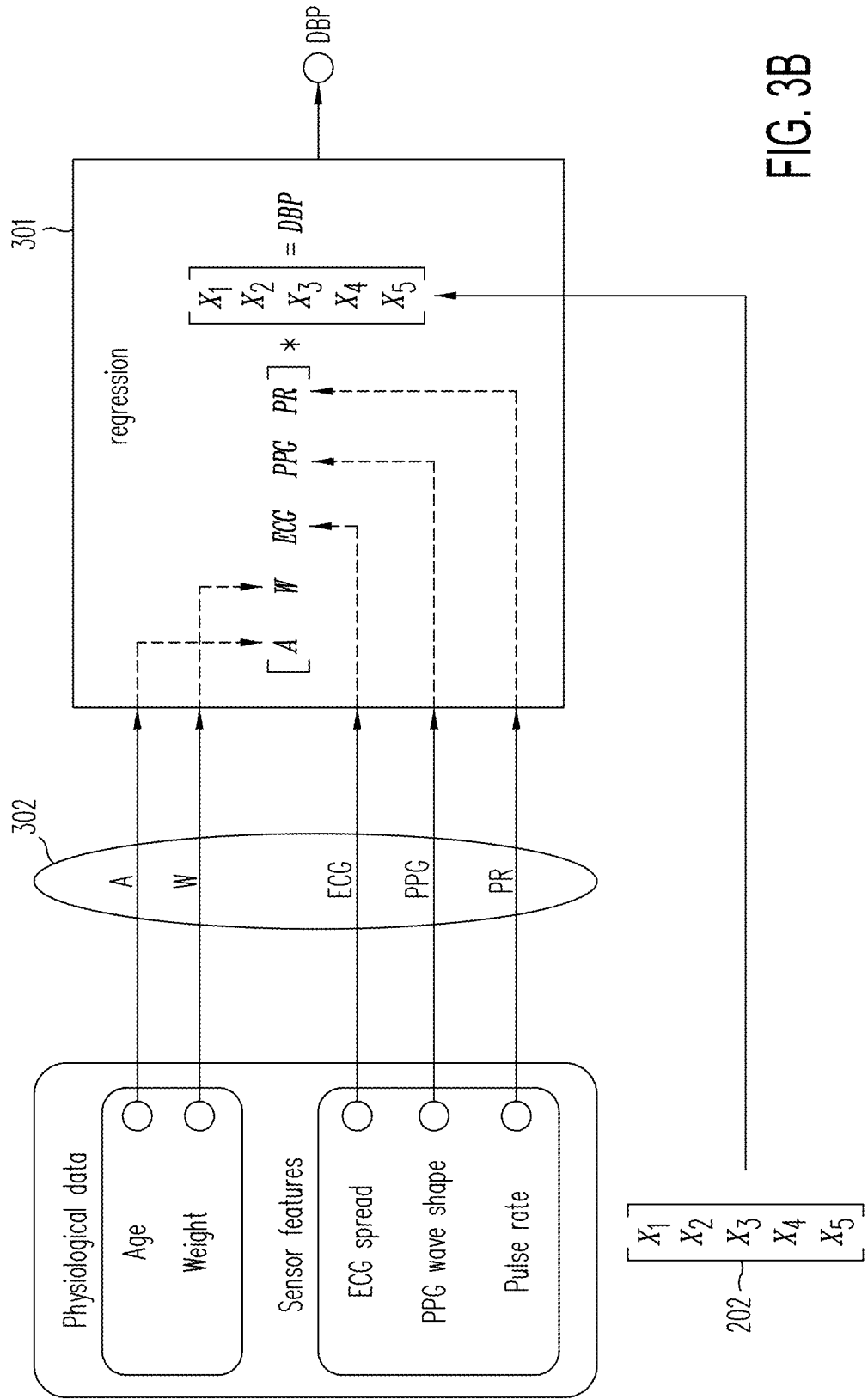
FIG. 3B illustrates a naïve diastolic blood pressure regression model for a test phase of the blood pressure predictor with physiological data.

Referring now to FIG. 3B, during a test phase, a measurement M 302

$$M=[A \; W \; ECG \; PPG \; PR]$$

is provided to the algorithm along with the previously learned X vector 202 of coefficients from the learning or training mode. The X vector 202 of coefficients in transpose matrix form are $$X^T=[X_1 \; X_2 \; X_3 \; X_4 \; X_5]$$

To calculate the diastolic blood pressure (DBP) with the blood pressure equation, the measurement M from a user of the vital signs scanner is multiplied by the learned X vector of coefficients as in the following equation $$M*X=DBP$$

A system for estimating blood pressure, using both physiological data and sensory features, shows improvement in accuracy over previous systems. However, predicting SBP or DBP with medical precision still requires recalibration over time as the user's physiology changes.

Augmenting Sensory Data by Mapping them into Physiological Models

The present invention exploits some of these biophysically-informed nonlinear equations and principles by injecting them back into the model in the form of nonlinear transformations. Physiological inputs may include subject age, approximate weight, height and gender. The parameters of the model are estimated from training data associating the input data with a set of gold-standard, cuff-based measurements.

Yet an additional inventive step is to augment the physiological+sensory data with mathematical models translating known physical formulas into the resolution space of this invention. These mathematical models include functions such as the natural logarithm ln x, or $$\frac{1}{x}$$

or other power transformations such as $$\frac{1}{x^2}.$$

They are used to model physical/physiological blood flow in the circulatory system such as the Moens-Korteweg equation which expresses the pressure P as a function of the square of PWTT: $P \propto f(PWTT^2)$, and the Bernoulli principle which expresses the pressure as a function $$P \propto \frac{a}{PWTT^2} + b \ldots$$

These physical/physiological models are abstracted away and introduced as non-linear equations through a non-linear transformation of input variables through h(.) and g(.) functions (respectively (406 and 407), an exemplary implementation of these functions might be:

$$h(x)=x^a$$

$$g(x)=\log(x*a)$$

where the value a is determined for each input value x, according to physical/physiological models from scientific literature.

For example, the Bernoulli principle can be entered into the linear regression for the calculation of the systolic blood pressure SBP using the PWTT input with the non-linear modifying function h:

$$SBP=h(PWTT)=PWTT^{-2}$$

In this case, the factor a is negative two (−2). An additional factor b is automatically generated by the linear regression when optimizing the X vector to finally generate the equation $$SBP=h(PWTT)=PWTT^{-2}+b$$

FIG. 12 illustrates experimental results corresponding to this Bernoulli principle linking Systolic blood pressure (SBP) to the PWTT. N curves 1202A-1202N represent a component of the function h for the measured or calculated PWTT. A particular one of the curves 1202A-1202N, such as curve 1202D for example, may be selected for a user in response to the physiological inputs that are associated with the given user. Knowing the PWTT for a user (e.g., 0.27 seconds) along the X-axis, a point 1204 on the curve 1202D may be selected for the given user. A component of the systolic blood pressure (e.g., 103 mmHg) may be determined from the Y-axis. This component of systolic blood pressure may be highly weighted over other components in the model.

Other components of the function h may be determined for other measured inputs, such as ECG spread, ECG spectral slope, PPG wave shape, and PPG spectral slope, and physiological inputs that may be weighted along with the PWTT component to determine components of the SBP. Other components of the function h may be determined for other measured inputs, such as ECG spread and PPG wave shape, and physiological inputs that may be weighted to determine components of the DBP. Mathematical equations may alternatively be used to estimate the experimental curves and the component of the function h for a given input.

FIG. 13 illustrates an exemplary relation for age, a component of the function g, linking systolic blood pressure to age. This relationship between age and SBP has been extensively studied. N curves 1302A-1302N represent a component of the function g for the physical input of age for the given user. Generally, the component of the function g for age:

$$SBP = g\text{ (age)} = \log(\text{age})$$

A particular one of the curves 1302A-1302N, such as curve 1302A for example, may be selected for a user in response to the physiological inputs that are associated with the given user. Knowing the age of the user (e.g., 33 years old) along the X-axis, a point 1304 on the curve 1302A may be selected for the given user. A component of the systolic blood pressure (e.g., 98 mmHg) may be determined from the Y-axis. This component of systolic blood pressure may be weighted with other components in the regression model and summed together to predict SBP for a given user. Similarly, components of diastolic blood pressure may be weighted in the regression model and summed together to predict DBP for a given user Other components of the function g may be determined for other physiological inputs (e.g., weight and height) and the measured inputs, then weighted to determine a component of the SBP and DBP. Mathematical equations may alternatively be used to estimate the experimental curves and the component of the function g for a given input. In either case, components of diastolic blood pressure may be weighted in a DBP regression model and summed together to predict DBP for a given user. In either case, components of systolic blood pressure may be weighted in a SBP regression model and summed together to predict SBP for a given user.

As such, the functions h and g are methods to introduce mathematical and/or experimental relations into the blood pressure prediction. The functional relations of h and g guide the regression algorithm towards physiologically valid solutions for predicting DBP and SBP by leveraging the medical state of the art. It is understood that the exemplary relations described above are only exemplary embodiments and that other components of h and g may be used in other embodiments.

The functional relations of h and g are key to one-time factory-based calibration of the vital signs scanner, since they contain the knowledge leading from sensory data (ECG related measurements, PPG related measurements, PWTT, Pulse rate . . . ) and physiological data (e.g. age, weight, height, gender . . . ) to systolic and diastolic blood pressure. The functions h and g are valid for a large population of people, without requiring any personal calibration.

Figure 4:
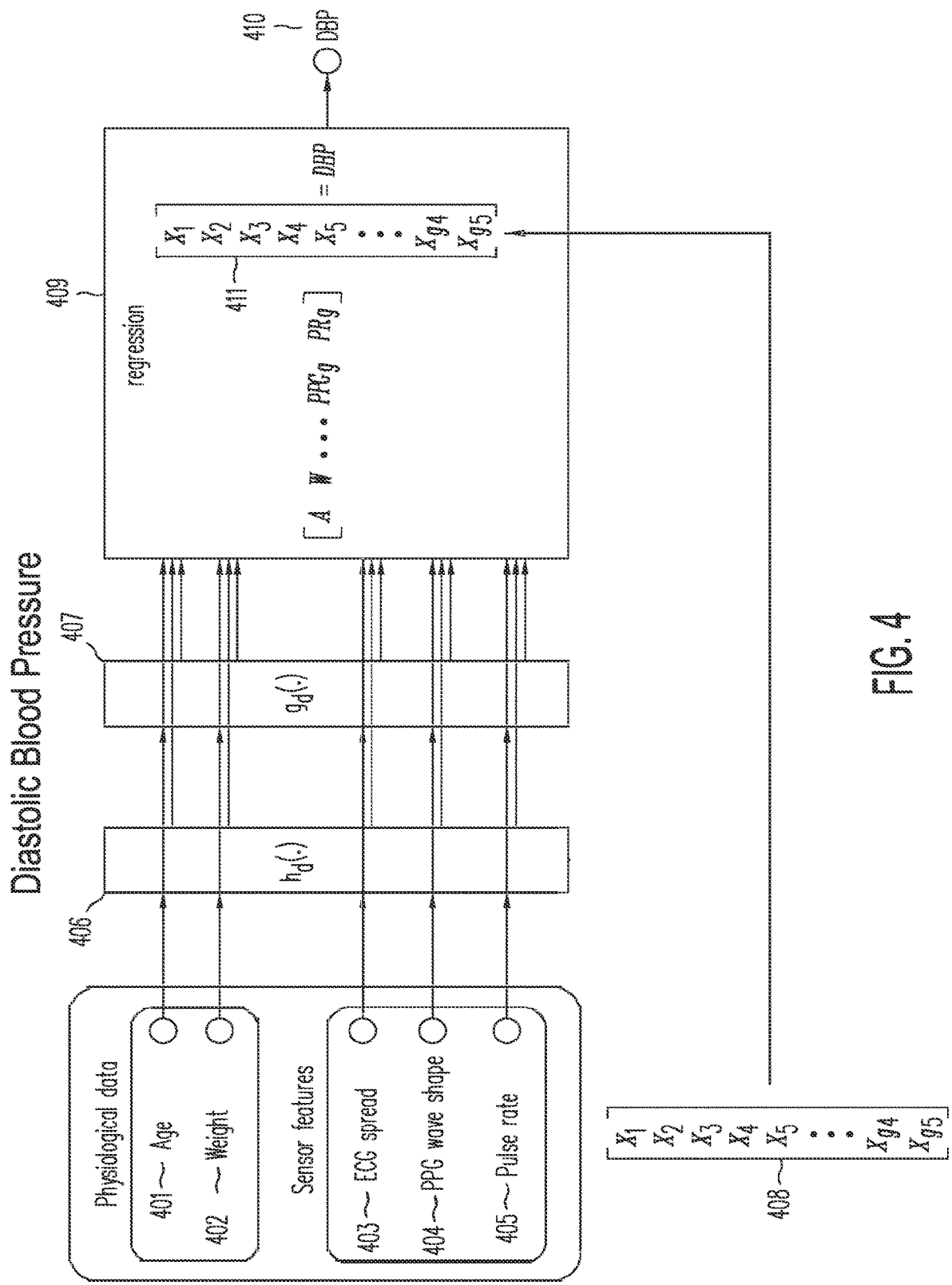
FIG. 4 illustrates a diastolic blood pressure regression model for the blood pressure predictor during a prediction phase.

FIG. 4 illustrates a regression model and method for calculating diastolic blood pressure of a user. The sensory input data is the ECG spread (403), the PPG wave-shape (404) and the pulse rate (405). Additional physiological data, such as age (401) and weight (402) of the user are other inputs into the regression model for calculating diastolic blood pressure of a user. The age (401) and weight (402) of the user are coupled into the functions $h_d$ (406) and $g_d$ (407) as well as for the regression model 409 to calculate diastolic blood pressure.

The output of the two functions $h_d$ (406) and $g_d$ (407) are coupled into the regression model. Examples of the two functions $h_d$ (406) and $g_d$ (407) are as follows:

$$A_h = h_d(\text{age}) = \text{age}^2$$

$$W_h = h_d(\text{weight}) = \frac{1}{\text{weight}}$$

-continued $$ECG_h = h_d(ECG \text{ spread}) = \frac{1}{ECG \text{ spread}}$$

$$PPG = h_d(PPG \text{ wave shape}) = \frac{1}{PPG \text{ wave shape}}$$

$$PR_h = h_d(\text{pulse rate}) = \frac{1}{\text{pulse rate}}$$

$$A_g = g_d(\text{age}) = \log(\text{age})$$

$$W_g = g_d(\text{weight}) = \log(\text{weight})$$

Non-linear partial model elements corresponding to each of the variables are generated. These model elements are stitched together by the DBP regression 409. The learned the optimal vector X (408) uses the best set of relations to predict the Diastolic Blood Pressure (410). The learning or training need only be performed once, when the algorithms are factory-calibrated prior to shipping of the vital signs scanner. With the physiological data, the learning and calibration can be independent from the end-user.

During normal use, the algorithm works in test mode solving the following equation (411):

$$M * X = DBP$$

where $M = [A \ W \ ECG \ PPG \ PR \ A_h \ W_h \ ECG_h \ PPG_h$
$PR_h \ A_g \ W_g]$ and $$X^T = [X_1 \ X_2 \ X_3 \ X_4 \ X_5 \ X_{h1} \ X_{h2} \ X_{h3} \ X_{h4} \ X_{h5} \ X_{g1} \ X_{g2}]$$

Figure 5:
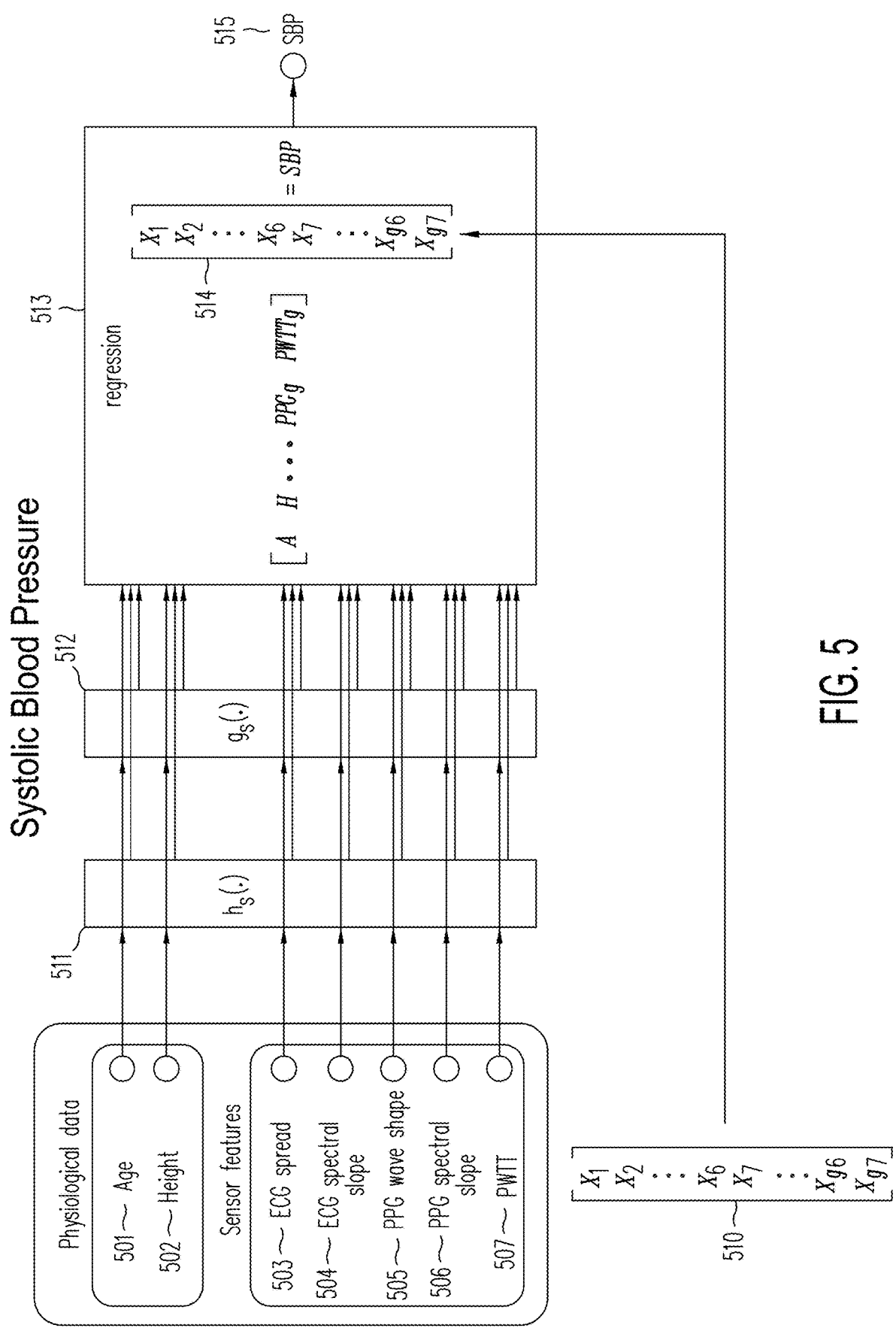
FIG. 5 illustrates a systolic blood pressure regression model for the blood pressure predictor during a prediction phase.

In the same manner, FIG. 5 illustrates a method of calculating systolic blood pressure with a regression algorithm. The sensory input data takes the ECG spread (503), the ECG spectral slope (504), PPG wave shape (505), PPG spectral slope (506) and, PWTT (507). Additional physiological data such as age (501) and height (502) of the patient are added for consideration by the regression model to predict systolic blood pressure. This can be translated into the vector $M_m$ as follows:

$$M_m = [A \ H \ ECG \ ECG\_SL \ PPG\_WS \ PPG\_SL \ PWTT]$$

To extend these data towards including physiological models, examples of the two functions $h_d$ (511) and $g_d$ (512) are as follows:

For $h_d$ (511):

$$A_h = h_s(\text{age}) = \frac{1}{\text{age}}$$

$$H_h = h_s(\text{height}) = \frac{1}{\text{height}}$$

$$ECG_h = h_s(ECG \text{ spread}) = \frac{1}{ECG \text{ spread}}$$

$$ECG\_SL_h = h_s(ECG \text{ spectral slope}) = \frac{1}{ECG \text{ spectral slope}}$$

$$PPG\_WS_h = h_s(PPG \text{ wave shape}) = \frac{1}{PPG \text{ wave shape}}$$

$$PPG\_SL_{f_h} = h_s(PPG \text{ spectral slope}) = \frac{1}{PPG \text{ spectral slope}}$$

$$PWTT_h = h_s(PWTT) = \frac{1}{PWTT^2}$$

For $g_d$ (512):

$$A_g = g_d(\text{age}) = \log(\text{age})$$

$$H_g = g_s(\text{height}) = \log(\text{height})$$

$$ECG_g = g_s(ECG \text{ spread}) = \log(ECG \text{ spread})$$

$$ECG\_SL_g = g_s(ECG \text{ spectral slope}) = \log(-ECG \text{ spectral slope})$$

$$PPG\_WS_g = g_s(PPG \text{ wave shape}) = \log(PPG \text{ wave shape})$$

$$PPG\_SL_g = g_s(PPG \text{ spectral slope}) = \log(-PPG \text{ spectral slope})$$

$$PWTT_g = g_s(PWTT) = \log(PWTT)$$

Non-linear partial model elements corresponding to each of the variables can be generated. These model elements are stitched together with $M_m$ by the SBP regression 513. The optimal vector X (510) is learned or trained during an initialization process. The optimal vector X (510 represents the best set of relations to predict the Systolic Blood Pressure (515) in response to the measured and physiological inputs. The training need only be performed once, when the algorithms are factory-calibrated prior to shipping. Accordingly, the learning and calibration can be performed independent of the end-user.

During normal use, the algorithm works in an operational or test mode solving the following equation (514):

$$M*X=SBP$$

where $$M=[A \: H \: ECG \ldots PWTT \: A_h \: H_h \ldots PWTT_h \: A_g \: H_g \ldots PWTT_g]$$

and $$X^T=[X_1 \: X_2 \ldots X_6 \: X_7 \: X_{h1} \: X_{h2} \ldots X_{h6} \: X_{h7} \: X_{g1} \: X_{g2} \ldots X_{g6} \: X_{g7}]$$

FIG. 14 illustrates the transpose of matrix M ($M^T$) and the matrix X in table form.

While example components of the functions of h and g have been described in some detail, another function f 153B may be used to generate components for SBP and/or DBP that is based on sensor features alone, as is shown in FIG. 1D. In this case, the individual values for the X vector associated with the physiological inputs may be set to zero when multiplied by the physiological input components for SBP and/or DBP. Similarly, a component of the function g may only be based on a physiological input and not a sensory input. Accordingly, the individual values for the X vector associated with the physiological input may be set to zero when multiplied by the sensor measured input components for SBP and/or DBP. In other words, the weighting may be zero in this case.

Determining PWTT by Cross-Correlation of Signals

Figure 11:
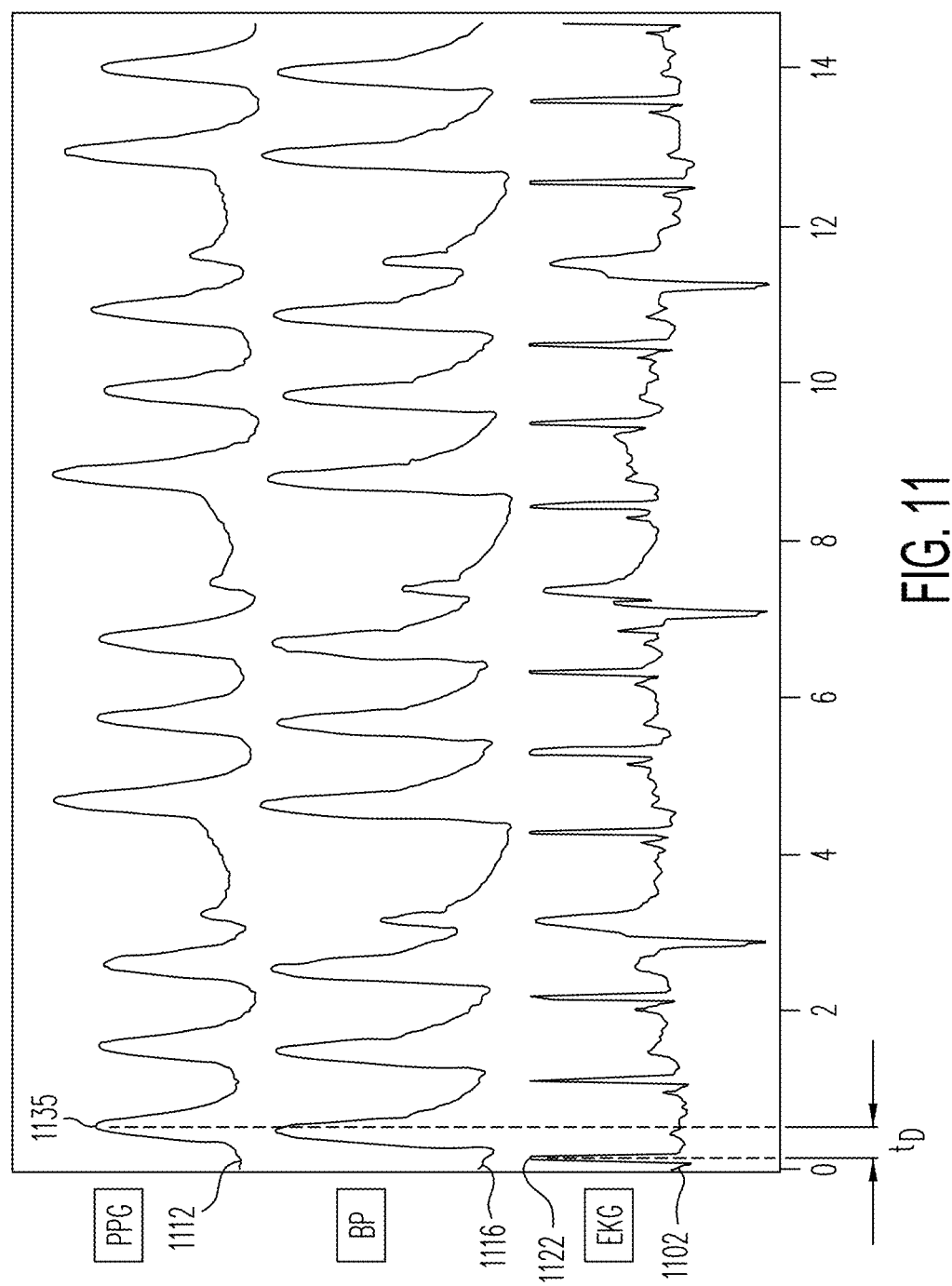
FIG. 11 illustrates a graph of an exemplary PPG waveform, an exemplary ECG waveform, and an exemplary blood pressure waveform for the same person aligned in time together.

Referring now to FIG. 11, PPG signals 1112 and ECG (or EKG) signals 1102 are often used to extract a PWTT to estimate SBP and DBP in a blood pressure (BP) signal 16. The calculation of the PWTT value is typically based on the time differences between the peaks in the ECG signal 1102 and the PPG signal 1112, such as the time difference $t_D$ between the ECG peak 1122 and the PPG peak 1135, for example.

Generally, ECG features are extracted from the ECG signal 802, including the R of the QRS complex 800, shown in FIGS. 8A-8B. FIGS. 8A-8B illustrate the relationship of the QRS complex to diastolic and systolic blood pressure. The peak feature 1135 (or rise time) in the PPG 1112 signal shown in FIG. 11 is typically determined by a peak detector, for example. However, these peak extracted features from the ECG and PPG signals are based on local properties. Thus, the position or time points of the peaks are approximately determined and sensitive to noise. Moreover, the PWTT value is sensitive to how the ECG signal 1102 and the PPG signal 1112 are aligned for comparison. A total PWTT error, for the PWTT calculated from the peak features of ECG and PPG signals, is the sum of the errors from peak extraction plus the errors in the peak alignment algorithm that is used to align the ECG and PPG signals. Accordingly, aligning the ECG and PPG signals, determining peak features in each, and determining a difference in peak values to determine PWTT can lead to low precision values that are not very usable.

The embodiments of the invention employ cross-correlation of the ECG and PPG signals instead to determine a PWTT value and improve its accuracy and the accuracy of systolic blood pressure measurements. The embodiments of the invention employ auto-correlation of the PPG signal to determine a pulse rate value and improve the accuracy of diastolic blood pressure measurements.

Referring now to FIGS. 1C, 6A-6B, and 7A-7B a plurality of signal waveforms are illustrated to explain how the cross-correlation algorithm employed by the cross-correlator 104 can increase precision of ECG measurements. The ECG and the PPG signals concurrently captured by the respective sensors 50 of the vital signs scanner 902 are processed concurrently in parallel together by the signal processor 52.

A raw ECG signal is received from an ECG sensor. The raw ECG signal received from the ECG sensor is filtered by the filter 101 and normalized by the normalizer 102 to generate the normalized ECG signal x(t) 602.

Similarly, a raw PPG signal is received from a PPG sensor. Concurrently in parallel, the raw PPG signal received from the PPG sensor is filtered by the FIR filter 111 and normalized by the normalizer 112 to generate the normalized PPG signal 612.

The normalized ECG signal x(t) 602 goes through an L1 trend filter 103 and a normalizer 103A to generate the normalized L1 trend signal 603. The normalized L1 trend signal 603 is coupled into a fast Fourier transformer 103B to put it into the frequency domain so that it is ready to be coupled into the cross-correlator 104 to undergo the cross correlation process 604 with the PPG related signal 614.

In parallel, the normalized PPG signal 612 undergoes a differential process by the differentiator to generate the differentiated PPG signal 613. The differential PPG signal 613 is coupled into the L1 trend filter 114A and then into the normalizer to generate the normalized trending differential PPG signal 614. The normalized trending differential PPG signal 614 is coupled into a fast Fourier transformer 114B to put it into the frequency domain so that it is ready to be coupled into the cross-correlator 104 to undergo the cross correlation process 604 with the ECG related signal 603.

The cross correlation process 604 is performed in the frequency domain using the transformed differential PPG signal 614 and the transformed ECG signal 603. FIG. 10A illustrates waveforms to show the cross correlation process between an f signal waveform 1002 and a g signal waveform 1003 to form the resultant cross-correlation waveform 1004. The cross-correlation 604 between the normalized trending differential PPG signal 614 and the normalized L1 trend signal 603 in the frequency domain results in a continuous time varying signal, referred to as the cross-correlation signal 615.

Figure 6B:
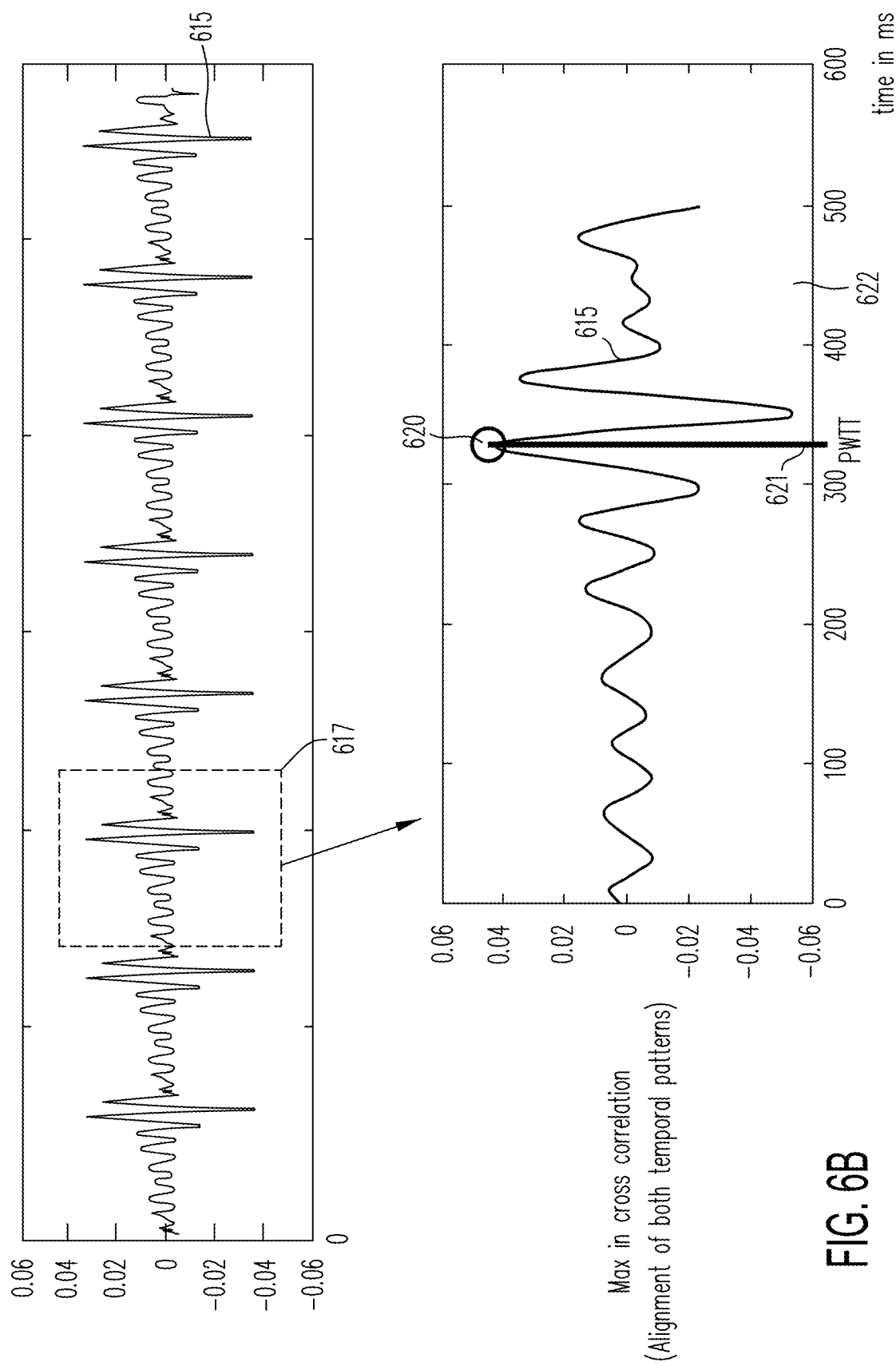

Referring to FIG. 6B, generally the cross-correlation algorithm finds the best matching pattern between the temporal pattern tp(g) in the ECG signal 605 and the temporal pattern tp(p) in the PPG signal. With a best match between temporal patterns, a precise offset time between ECG and PPG can be determined that represents the desired PWTT value.

The cross-correlation signal 615 is coupled into the maximum peak detector 104B to extract the PWTT value that corresponds to the maximum peak value 620 of the cross-correlation function 604. A window 617 in the cross-correlation signal 615 associated with the maximum peak 620 is show in FIG. 6B. The maximum peak value 620 in the cross-correlation signal 615 is at a time point 622 in the time domain or space. The time scale against which the cross-correlation signal 615 is plotted is in milliseconds and the maximum peak value 620 from a minimum peak value is at a time point of about three hundred twenty five milliseconds, for example.

In the embodiments of the invention, the cross correlation 604 considers the ECG signal and the PPG signal captured in their entirety during the measurement period of the vital signs scanner. Considering the ECG signal and the PPG signal in their entirety, takes into consideration thousands (e.g., n greater than or equal to 1000) of sampling points. Previous methods used in the prior art only used a few (e.g., n=2 to 8) time points of peaks or other localized signal features extracted from the PPG and ECG signals. Due to imprecision and errors in feature extractions from the ECG signal and the PPG signal and the low number of sampling time points, the prior art methods of PWTT calculation are easily corrupted by noise or other artifacts in the data and prove to be unreliable in the field.

The cross correlation function 604 performed by cross correlator 104 in the embodiments of the invention considers the L1 trend ECG waveform 603 and the L1 trend diff PPG waveform 614 in their entirety, taking into consideration thousands of sampling points over the measurement time period of the scanning device. As a result, the cross-correlation waveform 615 is highly robust to noise or distortions in either the ECG signal or the PPG signal. Moreover, noise that is common to both normalized ECG and PPG waveforms can enhance the cross-correlation because both sensors are capturing signals from the same location within the same hardware device. Noise in this case, that would hamper previously used methods, is being taken advantage by the embodiments of the invention.

Additionally, finer time resolution than the sampling interval can be obtained from the cross-correlation function provided by the cross-correlator, simply by fitting a quadratic or cubic polynomial model to the largest peak in the cross correlation function, and computing the time point of the maximum peak correlation from this polynomial model analytically. Therefore, the method of cross-correlation employed by embodiments of the invention has both a significantly higher timing precision than existing methods, and is far more robust to noise or other corruption in the ECG and PPG signals. The cross-correlation function in the signal analysis system is one key aspect to a self-calibration method for determining measures of blood pressure.

Referring now to FIGS. 7A-7B, exemplary signals x(t), q(t), p(t) and r(t) are shown respectively for a male (Caucasian male) and for a female (Asian female). The x(t) signal shown in FIGS. 7A-7B is the input ECG signal waveform that is captured by the sensors and coupled into the signal processor. The q(t) signal waveform is the estimated QRS complex signal waveform derived from the ECG signal waveform x(t). The p(t) signal waveform is the filtered and differentiated PPG signal waveform generated by the differentiator 113 shown in FIG. 1C. The r(t) signal waveform is the result of the cross-correlation between the x(t) signal waveform and the p(t) signal waveform by the cross-correlator 104 shown in FIG. 1C. Location of the maximum positive r(t) value in the curve corresponds to the desired PWTT value. This value of PWTT obtained by cross-correlation is more accurate than other methods and is used to determine more accurate values for SBP and DBP.

The resulting blood pressure predictions for SBP and DBP from the model in the second stage of the signal analysis system are sufficiently accurate such that they are competitive with cuff-based measurements. The prediction error for SBP and DBP made by embodiments of the invention fall within the range of industry standard guidelines for clinical-grade blood pressure measurement. With a device employing the algorithms and methods described herein, a combined ECG/PPG-derived blood pressure measurement is practical for a portable vital signs scanner and the vital signs scanning system.

Portable Vital Signs Scanner and Vital Signs Scanning System

Figure 9A:
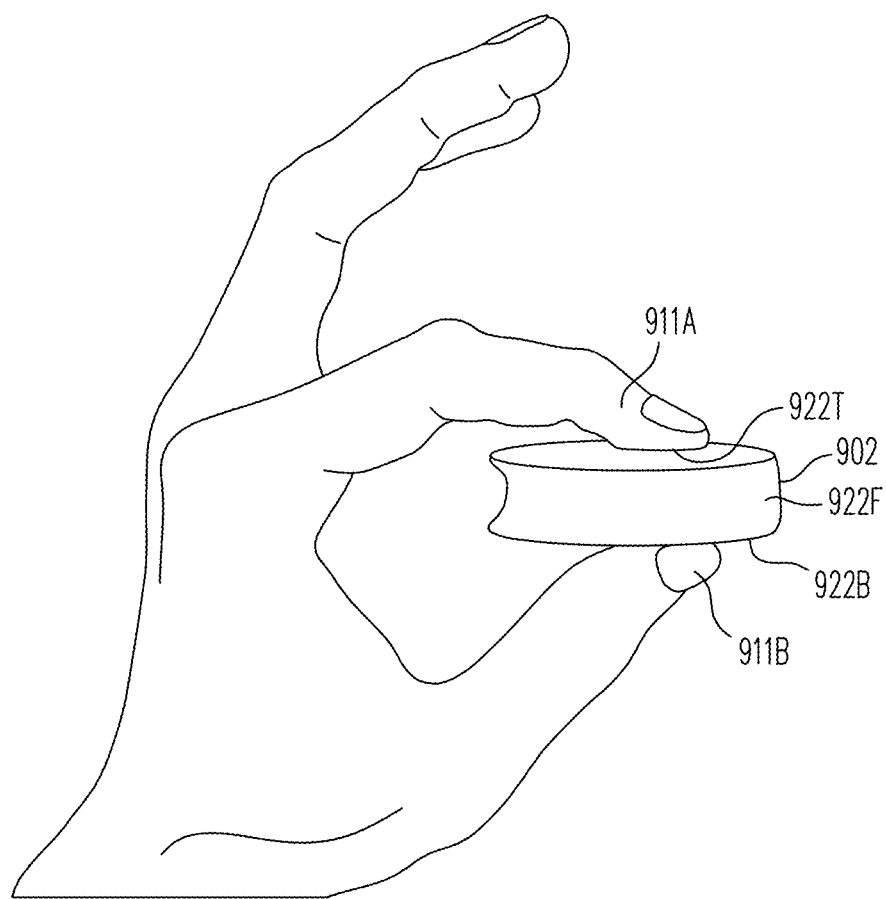
FIG. 9A is a diagram illustrating an exemplary vital signs scanning system with the scanner held at the forehead/temple.

Referring now to FIG. 9A, a hand held portable vital signs scanner 902 to scan for vital signs is shown. The hand held vital signs scanner 902 includes at least one ECG (electrocardiogram) sensor and at least one PPG (photoplethysmogram) sensor. The PPG sensor and one electrode 922F of the ECG sensor is found at the front side of the scanner 902. A second electrode 922B of the ECG sensor in the scanner 902 is found at the bottom or top of the scanner 902.

To take a blood pressure reading, the user contacts the front side electrode 922F with the user's temple or forehead. With the thumb finger 911B in contact with the bottom electrode 922B (alternatively the index finger 911A with a top electrode 921T), a circuit may be formed through the finger and the hand of the user and a portion of his body back to the front side electrode 922F.

Figure 9B:
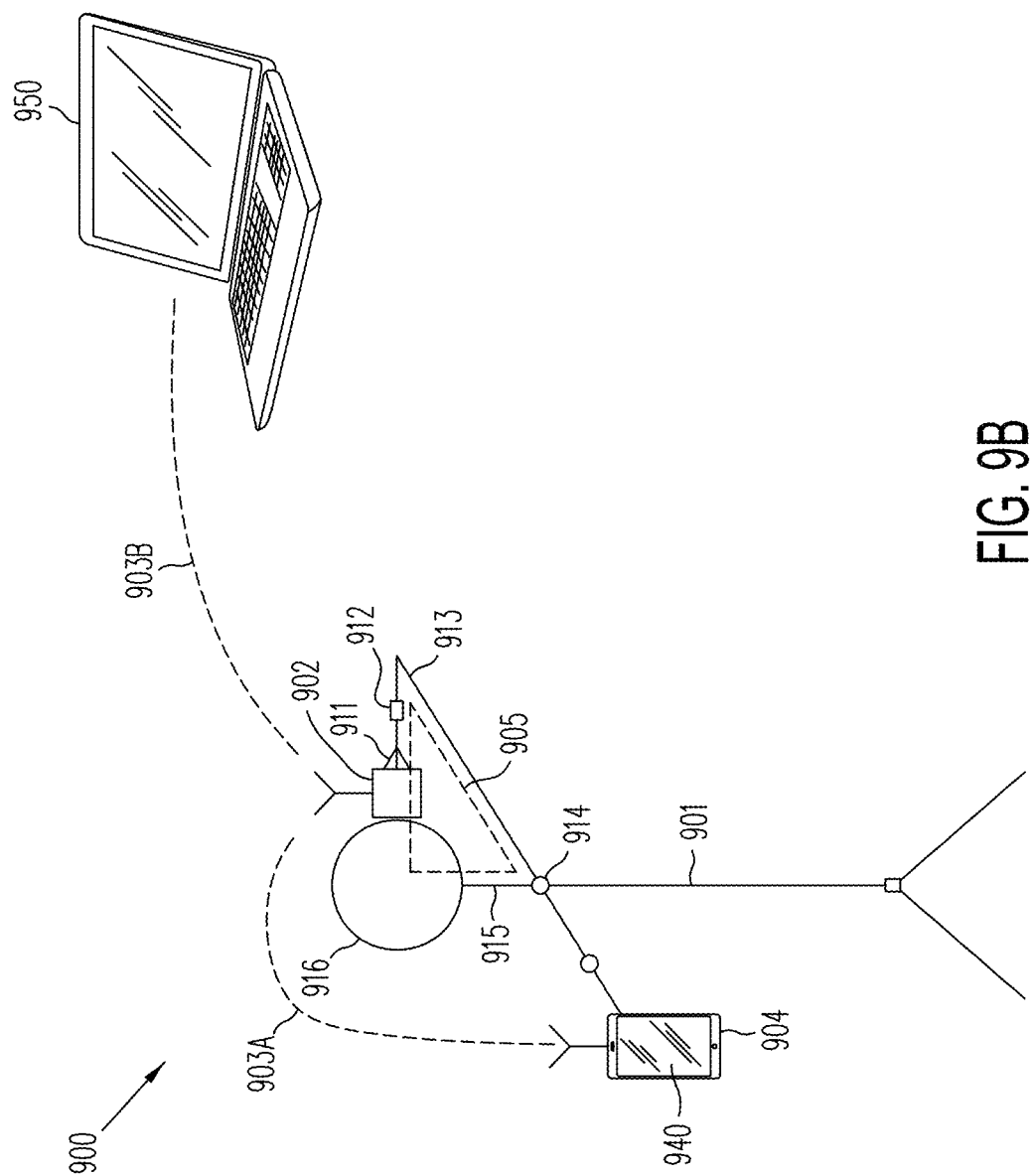
FIG. 9B is a perspective view of a user squeezing the exemplary vital signs scanner.

FIG. 9B illustrates a vital signs scanning system 900 including the vital signs scanner 902 and a portable electronic device 904 in wireless communication 103A together. The vital signs scanning system 900 may also include a computer 950 in wireless communication with the vital signs scanner 902.

FIG. 9B further illustrates the positioning of the scanner 902 next to the body of the user 901 so that the front side electrode 922F of the vital signs scanner makes contact with the user's temple or forehead. With the vital signs scanner 902 near the user's temple or forehead, the vital signs scanner 902 can measure his/her blood pressure. Concurrent ECG and PPG readings are used by the vital signs scanner 902 to determine the Pulse Wave Transit Time (PWTT). PWTT is directly related to blood pressure.

Referring to FIGS. 9A-9B, the portable vital signs scanner 902 measures PPG from the user's temple or forehead. Concurrently, the portable vital signs scanner 902 measures ECG between the two electrodes of the ECG sensor, electrode 922F in contact with the user's temple and electrode 922B (or electrode 922T) in contact with the user's finger 911B (or 911A). Measuring PPG at the human temple takes advantage of human anatomy.

Figure 9C:
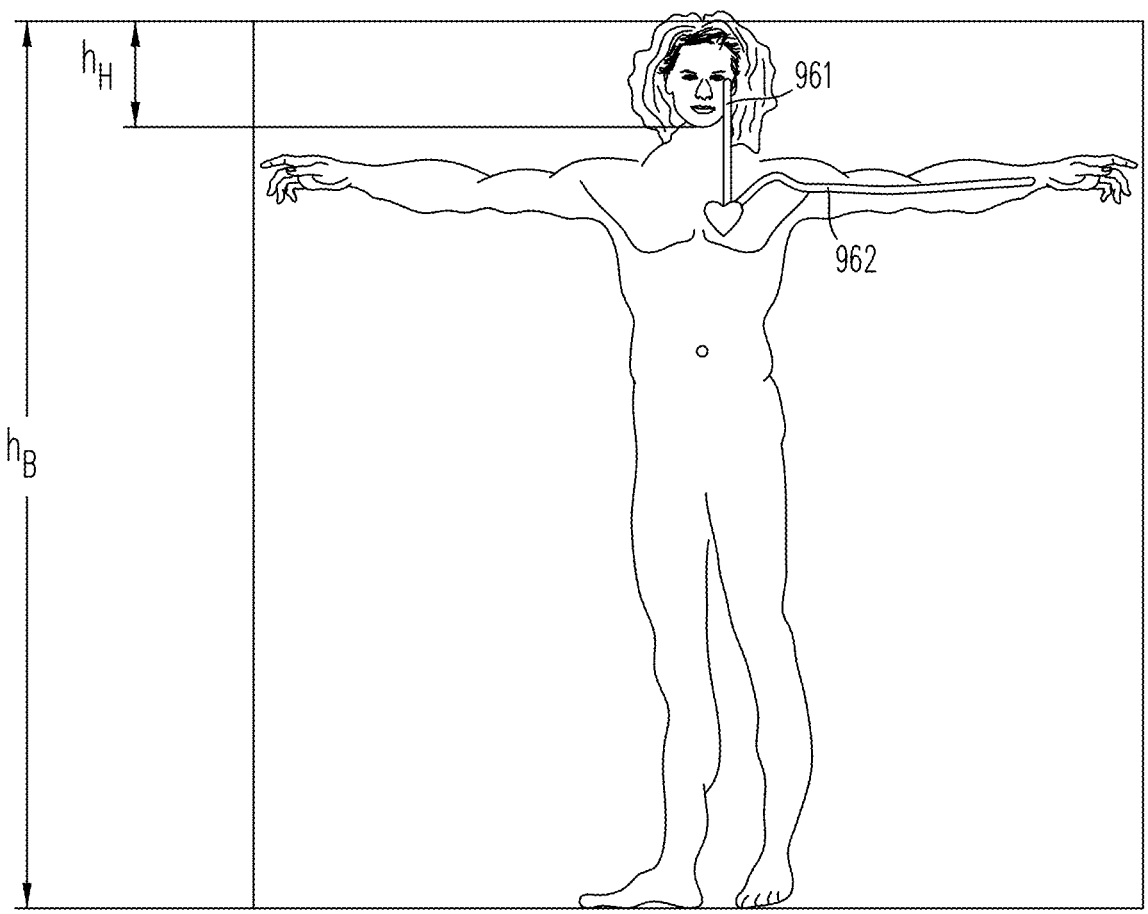
FIG. 9C. is a diagram illustrating preferred measurement locations on a body.

FIG. 9C illustrates physiological properties of body height $h_B$ and head heath $h_H$ of the human body. The head-to-body ratio ($h_H/h_B$) is approximately constant (e.g., head/body ratio=1/7, with insignificant standard deviation) from user to user. In contrast, the distance from the user's heart to a classic blood pressure site on the arm or wrist is highly variable (with a high standard deviation) and is proportional to the height $h_B$ of the individual. Consequently there are fewer variations in physiological proportions between thorax/head than the length of arms (where a blood pressure cuff is typically used). That is, there is less physiological variability in the PWTT and other derived vital signs measurements between individuals when taking measurements at the user's temple and at the user's finger of the left hand.

In addition, the artery 961 from a human heart to the temple is shorter than the artery 962 from the human heart through the arm to the wrist. Accordingly, the artery 961 from the user's heart to the user's temple is not subject to severe pressure drops that may be experienced with measurements that are performed on the user's arms or at the user's wrists. Vital signs measurements performed on the user's arms or wrists vary in a complex way according to many factors. For example, vital signs measurements can vary as a function of the geometric configuration of the arms, and the tension in the bulkier muscle groups such as the triceps and deltoids. The blood flow in the arm drops due to arm bending.

Referring now to FIGS. 9A-9B, unlike traditional blood pressure measuring devices using PWTT wherein the ECG is taken at the patient's leg or trunk, the vital signs scanner 902 forms an electronic circuit 905 from the user's hand 912, through the arm 913, heart 914, neck 915, into the head 916 and up to the user's temple. The positioning of the electrode 922F at the temple and the other at a finger of the hand 912 decreases the errors in the timing of the PPG. Blood flow goes directly to the temple from the aorta, without the motions and complexity of arm and finger circulations.

Furthermore, the vital signs scanner 902 doesn't need repeated recalibration after it has been initially trained to a given user after capturing the initial parameters. The scanner calibrates blood pressure based on a large database of people. Thus, the vital signs scanner 902 does not need the traditional pressure cuff used in the auscultatory and oscillometric methods of non-invasive blood pressure readings.

Additionally, the method of measuring blood pressure that is employed by the embodiments of the invention brings anatomical variations back into the measurements, by accounting for physiological data inputs including subject age, approximate weight, height, gender, etc.

Further details of the scanner 902 and its system 900 of use are illustrated and described in "METHODS OF DATA ACQUISITION QUALITY AND DATA FUSION FOR PERSONAL PORTABLE WIRELESS VITAL SIGNS SCANNER filed by Wenyi Zhao et al., on May 30, 2014 as U.S. Ser. No. 14/292,820 incorporated herein by reference.

CONCLUSION

When implemented in software, the elements of the embodiments are essentially the code segments of instructions that may be executed by one or more processors (e.g., signal processor 52 in FIG. 1B) to perform and carry out tasks and provide functionality. The program or code segments can be stored in a processor readable medium or storage device (e.g., memory 54,56 in FIG. 1B) that is coupled to or at least in communication with the one or more processors. The processor readable medium may include any medium or storage device that can store information. Examples of a processor readable medium include, but are not limited to, an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The program or code segments may be downloaded or transmitted by a computer data signal embodied in a carrier wave over a transmission medium or communication link. A computer data signal may include any signal that can propagate over a transmission medium such as electronic network channels, optical fibers, air, electromagnetic, RF links, etc. The program or code segments may be downloaded, for example, over computer networks such as the Internet, an intranet, etc.

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is limited only by patented claims that follow below.

What is claimed is:

1. A non-invasive method of measuring blood pressure, the method comprising:
   concurrently placing a PPG sensor of a portable cuffless blood pressure measuring device near a temple of a user and forming an electronic circuit with a first electrode and a second electrode of the portable cuffless blood pressure measuring device, wherein the electronic circuit is formed by contacting the first electrode to the temple and contacting the second electrode to a finger of the user holding the portable cuffless blood pressure measuring device;
   with the portable cuffless blood pressure measuring device, concurrently scanning for ECG data in response to the electronic circuit and PPG data in response to the PPG sensor positioned near the temple of the user;
   signal processing the ECG data to determine an ECG spread and an ECG spectral slope, and
   signal processing the PPG data to determine a PPG wave-shape and a PPG spectral slope;
   cross-correlating the ECG data and the PPG data to determine a pulse wave transit time (PWTT) of the user;
   receiving one or more physiological data of the user; and
   predicting systolic blood pressure of the user in response to the PWTT, the ECG spread, the ECG spectral slope, the PPG wave-shape, the PPG spectral slope and the one or more physiological data of the user.

2. The non-invasive method of claim 1, wherein the one or more physiological data of the user is one or more of age, gender, height, weight, and body mass.

3. The non-invasive method of claim 1, wherein prior to the cross-correlating the method further comprises:
signal processing the PPG data and the ECG data to reduce noise.

4. The non-invasive method of claim 1, further comprising:
auto-correlating the PPG data to determine a pulse rate; and
predicting diastolic blood pressure of the user in response to the pulse rate and the one or more physiological data of the user.

5. The non-invasive method of claim 4, wherein,
the one or more physiological data of the user is one or more of age, gender, height, weight, and body mass.

6. The non-invasive method of claim 1, wherein,
The predicting of the systolic blood pressure of the user is performed by regression analysis of the PWTT, the ECG spread, the ECG spectral slope, the PPG wave-shape, the PPG spectral slope, and the one or more physiological data of the user.

7. The non-invasive method of claim 4, wherein,
the predicting of the systolic blood pressure of the user is performed by a first regression analysis of the PWTT, the ECG spread, the ECG spectral slope, the PPG wave-shape, the PPG spectral slope and the one or more physiological data of the user; and
the predicting of the diastolic blood pressure of the user is performed by a second regression analysis of the pulse rate and the one or more physiological data of the user.

8. The non-invasive method of claim 4, wherein,
the predicting of the diastolic blood pressure of the user is performed by a regression analysis of the pulse rate, the ECG spread, the ECG spectral slope, the PPG wave-shape, the PPG spectral slope, and the one or more physiological data of the user.

9. The non-invasive method of claim 7, further comprising
training user coefficients for the first regression analysis to predict the systolic blood pressure of the user in response to the PWTT, the ECG spread, the ECG spectral slope, the PPG wave-shape, the PPG spectral slope and the one or more physiological data of the user; and
training user coefficients for the second regression analysis to predict the diastolic blood pressure of the user in response to the pulse rate and the one or more physiological data of the user.

10. The non-invasive method of claim 9, wherein the training comprises:
measuring a measured systolic blood pressure and a measured diastolic blood pressure of the user;
comparing an initial predicted systolic blood pressure of the user with the measured systolic blood pressure of the user to determine the user coefficients for the first regression analysis to minimize a difference between the initial predicted systolic blood pressure and the initial measured systolic blood pressure of the user; and
comparing an initial predicted diastolic blood pressure of the user with the measured diastolic blood pressure of the user to determine the user coefficients for the second regression analysis to minimize a difference between the initial predicted diastolic blood pressure and the initial measured diastolic blood pressure of the user.

11. The non-invasive method of claim 10, wherein,
the training further includes the receiving of the one or more physiological data of the user.

12. A non-invasive method of measuring blood pressure, the method comprising:
concurrently placing a PPG sensor of a portable cuffless blood pressure measuring device near a temple of a user and forming an electronic circuit with a first electrode and a second electrode of the portable cuffless blood pressure measuring device, wherein the electronic circuit is formed by contacting the first electrode to the temple and contacting the second electrode to a finger of the user holding the portable cuffless blood pressure measuring device;
with the portable cuffless blood pressure measuring device, concurrently scanning for ECG data in response to the electronic circuit and PPG data in response to the PPG sensor positioned near the temple of the user;
signal processing the ECG data to determine an ECG spread and an ECG spectral slope, and
signal processing the PPG data to determine a PPG wave-shape and a PPG spectral slope;
auto-correlating the PPG data to determine a pulse rate of the user;
cross-correlating the ECG data and the PPG data to determine a pulse wave transit time (PWTT) of the user;
receiving one or more physiological data of the user; and
predicting systolic blood pressure of the user in response to the PWTT and the one or more physiological data of the user; and
predicting diastolic blood pressure of the user in response to the pulse rate and the one or more physiological data of the user, wherein predicting the diastolic blood pressure of the user is performed by a regression analysis of the pulse rate, the ECG spread, the ECG spectral slope, the PPG wave-shape, the PPG spectral slope, and the one or more physiological data of the user.

13. The non-invasive method of claim 12, wherein,
the one or more physiological data of the user is one or more of age, gender, height, weight, and body mass.

* * * * *